(12) United States Patent
Khachigian

(10) Patent No.: US 7,541,343 B2
(45) Date of Patent: Jun. 2, 2009

(54) INHIBITING CELLULAR PROLIFERATION BY EXPRESSING YIN YANG-1

(75) Inventor: Levon Michael Khachigian, New South Wales (AU)

(73) Assignee: Newsouth Innovations Pty Limited, Sydney (AU)

( * ) Notice: Subject to any disclaimer, the term of this patent is extended or adjusted under 35 U.S.C. 154(b) by 0 days.

(21) Appl. No.: 10/478,488

(22) PCT Filed: May 21, 2002

(86) PCT No.: PCT/AU02/00629

§ 371 (c)(1),
(2), (4) Date: May 19, 2004

(87) PCT Pub. No.: WO02/094307

PCT Pub. Date: Nov. 28, 2002

(65) Prior Publication Data

US 2005/0054591 A1  Mar. 10, 2005

(30) Foreign Application Priority Data

May 22, 2001 (AU) .................................. PR5185

(51) Int. Cl.
*A01N 43/04* (2006.01)
*A01N 65/00* (2006.01)
*A61K 31/70* (2006.01)
*C12N 15/00* (2006.01)
*C12N 5/00* (2006.01)
*C12N 5/02* (2006.01)
*A61F 2/06* (2006.01)

(52) U.S. Cl. ..................... 514/44; 424/93.1; 435/320.1; 435/325; 623/1.1

(58) Field of Classification Search ........................ None
See application file for complete search history.

(56) References Cited

U.S. PATENT DOCUMENTS 5,856,121 A * 1/1999 Gorski et al. .............. 435/69.1

FOREIGN PATENT DOCUMENTS

| GB | 98/02885 | 2/1998 |
|---|---|---|
| WO | WO91/00047 | 1/1991 |
| WO | WO94/26914 | 11/1994 |
| WO | WO94/28152 | 11/1994 |
| WO | WO95/02697 | 1/1995 |
| WO | WO95-03400 | 2/1995 |
| WO | WO95/27071 | 10/1995 |
| WO | WO96/03508 | 2/1996 |
| WO | WO96/09400 | 3/1996 |
| WO | WO96/10088 | 4/1996 |
| WO | WO96/22378 | 7/1996 |
| WO | WO96/25506 | 8/1996 |
| WO | WO96/33623 | 10/1996 |
| WO | WO97/12622 | 4/1997 |
| WO | WO97/17457 | 5/1997 |
| WO | WO98/05754 | 2/1998 |
| WO | WO98/05759 | 2/1998 |
| WO | WO98/05854 | 2/1998 |
| WO | WO98/18815 | 5/1998 |
| WO | WO98/30707 | 7/1998 |

OTHER PUBLICATIONS

Meier, et al. (1994) Molecular and Cellular Biology, 14(1): 128-37.*
Zambrano, et al. (1997) Biochem. J., 328: 293-300.*
Thomas, et al. (1999) Gene, 236, 197-208, pp. 197-198.*
Shi, et al. (1997) Biochimica et Biophysica Acta, 1332: F49-F66.*
Verma et al. (1997) Nature, vol. 389, p. 239.*
Pfeifer and Verma (2001) Annu. Rev. Genomics. Hum. Genet. 2:177-211.*
Johnson-Saliba et al. (2001) Curr. Drug. Targets 2:371-99.*
Shoji et al. (2004) Current Pharmaceutical Design 10 :785-796.*
Lundberg, et al (1999) Experimental Gerontology, 34: 549-57.*
Newby, et al. (2000) Journal of Pathology, 190: 300-09.*
Hedin, et al. (1988) Journal of Cell Biology, 107: 307-19.*
Ace, et al, "Construction and Characterization of a Herpes Simplex Virus Type 1 Mutant Unable to Transinduce Immediate-Early Gene Expression", *J. Virol.* 63(5):2260-2269 (May 1989).
Bender, et al., "Evidence That the Packaging Signal of Moloney Murine Leukemia Virus Extends into the Gag Region", *J. Virol.* 61(5):1639-1646 (May 1987).
Blomer, et al. "Highly Efficient and Sustained Gene Transfer in Adult Neurons with a Lentivirus Vector" *J. Virol.* 71(9):6641-6649 (Sep. 1997).
Chou, and Roizman, The $\gamma_1$34.5 Gene Herpes Simplex Virus 1 Precludes Neuroblastoma Cells from Triggering Total Shutoff of Protein Synthesis Characteristic of Programmed Cell Death in Neural Cells, *PNAS* 89:3266-3270 (Apr. 1992).
Chou, et al. "Differential Response of Human Cells to Deletions and Stop Condons in the $\gamma_1$34.5 Gene of Herpes Simplex Virus" *J. Virol.* 68(12):8304-8311 (1994).
Coffin, et al., "Retroviruses" *HE Varmus*, Cold Spring Harbour Laboratory Press Eds.: J.M. Coffin, SM Hughes, pp. 758-763.
Coffin, et al., "Herpes Simplex Virus-Based Vectors" DS (ed). Genetic Manipulation of the Nervous System, Academic Press: London, pp. 99-114, (1996).
Cosset, et al. "High-Titer Packaging Cells Producing Recombinant Retroviruses Resistant to Human Serum" *J. Virol.* 69(12):7430-7436 (1995).
Cotton, et al. "Chicken Adenovirus (CELO Virus) Particles Augment Receptor-Mediated DNA Delivery to Mammalian Cells and Yield Exceptional Levels of Stable Transformants" *J. Virol.* 67(7):3777-3785 (1993).
Dedieu, et al., "Vectors for Gene Therapy of Cardiovascular Disease", *Curr Cardiol Rep.* 2(1):39-47 (Jan. 2000).
Fisher, et al., "Recombinant Adenovirus Deleted of all Viral Genes for Gene Therapy of Cystic Fibrosis" *Virology* 217:11-22 (1996).

(Continued)

*Primary Examiner*—Robert M Kelly
(74) *Attorney, Agent, or Firm*—DLA Piper LLP (US)

(57) ABSTRACT

The present invention provides a method of preventing or reducing cellular proliferation. The method involves administering to cells a composition which increases the level of YY1 protein, in particular YY1 mRNA, in the cells.

15 Claims, 3 Drawing Sheets

OTHER PUBLICATIONS

Gorziglia, et al., "Elmination of Both E1 and E2a from Adenovirus Vectors Further Improves Prospects for In Vivo Human Gene Therapy" *J. Virol.* 70(6):4173-4178 (1996).

Gosh-Choudhury, et al., "Human Adenovirus Cloning Vectors Based on Infectious Bacterial Plasmides" *Gene* 50:161-171 (1986).

Hiltunen, et al. Insights into the Molecular Pathogenesis of Atherosclerosis and Therapeutic Strategies Using Gene Transfer, *Vasc Med.* 5:41-48 (2000).

Kim, et al., "Minimal Requirement for a Lentivirus Vector Based on Human Immunodeficiency Virus Type 1" J. Virol. 72(1):811-816 (1998).

Fallaux, et al., "Characterization of 911:A New Helper Cell Line for the Titration and Propagation of Early Region 1-Deleted Adenoviral Vectors" *Hum. Gen. Ther.* 7:215-222 (Jan. 1996).

Krougliak, et al., "Development of Cell Lines Capable of Complementing E1, E4, and Protein IX Defective Adenovirus Type 5 Mutants" *Hum. Gen. Ther.* 6:1575-1586 (1995).

Laitinen, et al., "Vascular Gene Transfer for the Treatment of Restenosis and Atherosclerosis" *Curr Opin Lipidol* 9(5):465-469 (Oct. 1998).

Lieber, et al., "Recombinant Adenoviruses with Large Deletions Generated by Cred-Mediated Excision Exhibit Different Biological Properties Compared with First-Generation Vectors in Vitro and In Vivo" *J Virol.* 70(12):8944-8960 (Dec. 1996).

Levrero, et al., "Defective and Nondefective Adenovirus Vectors for Expressing Foreign Genes In Vitro and In Vivo" *Gene* 101:195-202 (1991).

MacLean, et al. "Herpes Simplex Virus Type 1 Deletion Variants 1714 and 1716 Pinpoint Neurovirulence-Related Sequences in Glasgow Strain 17$^+$Between Immediate Early Gene 1 and the 'a' Sequence" *J. Gen. Virol.* 72:632-639 (1991).

O'Brien, et al. "Gene Therapy for Atherosclerotic Cardiovascular Disease: A Time for Optimism and Caution" *Mayo Clinic Proc* 75(8):831-834 (Aug. 2000).

Pear, et al. "Production of High-Titer Helper Free Retroviruses by Transient Transfection" *PNAS* 90:8392-8396 (Sep. 1993).

Ribault, et al., "Chimeric Smooth Muscle-Specific Enhancer/Promoters" *Circ. Res.* 88:468-475, (2001).

Rice and Knipe, "Genetic Evidence for Two Distinct Transactivation Functions of the Herpes Simplex Virus α Protein ICP27" *J. Virol.* 64(4):1704-1715 (1990).

Smith, et al., "Evidence That Herpes Simplex Virus Immediate Early Protein ICP27 Acts Post-Transcriptionally During Infection to Regulate Gene Expression" *Virology* 186:74-86 (1992).

Soneoka, et al., "A Transient Three-Plasmid Expression System for the Production of High Titer Retroviral Vectors" *Nucl. Acids Res.* 23(4):628-633 (1995).

Yeh, et al., "Efficient Dual Transcomplementation of Adenovirus E1 and E4 Regions from a 293-Derived Cell Line Expressing a Minimal E4 Functional Unit" *J. Virol.* 70(1):559 (1996).

Yla-Herttuala, et al., "Cardiovascular Gene Therapy" *Lancet* 355:213-222 (Jan. 2000).

Santiago, et al. "Induction of the Transcriptional Repressor Yin Yang-1 by Vascular Cell Injury", *The Journal of Biological Chemistry*, 2001.

* cited by examiner

SEQUENCE LISTING

```
<160> NUMBER OF SEQ ID NOS: 6

<210> SEQ ID NO 1
<211> LENGTH: 2353
<212> TYPE: DNA
<213> ORGANISM: Homo sapiens

<400> SEQUENCE: 1
cgccgagacg agcagcggcc gagcgagcgc gggcgcgggc gcaccgaggc gagggaggcg      60
gggaagcccc gccgccgccg ccccgcccgc cccttccccc gccgcccgcc ccctctcccc     120
ccgcccgctc gccgccttcc tccctctgcc ttccttcccc acggccggcc gcctcctcgc     180
ccgcccgccc gcagccgagg agccgaggcc gccgcggccg tggcggcgga gccctcagcc     240
atggcctcgg gcgacaccct ctacatcgcc acggacggct cggagatgcc ggccgagatc     300
gtggagctgc acgagatcga ggtggagacc atcccgtgg agaccatcga gaccacagtg      360
gtgggcgagg aggaggagga ggacgacgac gacgaggacg gcggcggtgg cgaccacggc     420
```

-continued

```
ggcggggcg gccacgggca cgccggccac caccaccacc accatcacca ccaccaccac      480
ccgcccatga tcgctctgca gccgctggtc accgacgacc cgacccaggt gcaccaccac      540
caggaggtga tcctggtgca gacgcgcgag gaggtggtgg gcggcgacga ctcggacggg      600
ctgcgcgccg aggacggctt cgaggatcag attctcatcc cggtgcccgc gccggccggc      660
ggcgacgacg actacattga acaaacgctg gtcaccgtgg cggcggccgg caagagcggc      720
ggcggcggct cgtcgtcgtc gggaggcggc cgcgtcaaga agggcggcgg caagaagagc      780
ggcaagaaga gttacctcag cggcggggcc ggcgcggcgg cgggcgcgg cgccgacccg      840 ggcaacaaga gtgggagca aagcaggtg cagatcaaga ccctggaggg cgagttctcg       900
gtcaccatgt ggtcctcaga tgaaaaaaaa gatattgacc atgagacagt ggttgaagaa      960
cagatcattg gagagaactc acctcctgat tattcagaat atatgacagg aaagaaactt     1020
cctcctggag gaatacctgg cattgacctc tcagatccca acaactggc agaatttgct     1080 agaatgaagc caagaaaaat taagaagat gatgctccaa gaacaatagc ttgccctcat      1140
aaaggctgca caaagatgtt cagggataac tcggccatga gaaacatct gcacacccac     1200 ggtcccagag tccacgtctg tgcagaatgt ggcaaagctt ttgttgagag ttcaaaacta     1260
aaacgacacc aactggttca tactggagag aagcccttc agtgcacgtt cgaaggctgt      1320
gggaaacgct tttcactgga cttcaatttg cgcacacatg tgcgaatcca taccggagac     1380
aggccctatg tgtgcccctt cgatggttgt aataagaagt ttgctcagtc aactaacctg     1440
aaatctcaca tcttaacaca tgctaaggcc aaaaacaacc agtgaaaaga agagagaaga     1500
cccttctcga ccacgggaag catcttccag aagtgtgatt gggaataaat atgcctctcc     1560
tttgtatatt atttctagga agaattttaa aaatgaatcc tacacaccta agggacatgt     1620
tttgataaag tagtaaaaat taaaaaaaa aaactttact aagatgacat tgctaagatg     1680
ctctatcttg ctctgtaatc tcgtttcaaa acacagtgt ttttgtaaag tgtggtccca      1740
acaggaggac aattcatgaa cttcgcatca aaagacaatt ctttatacaa cagtgctaaa     1800
aatgggactt ctttttcacat tcttataaat atgaagctca cctgttgctt acaatttttt     1860
taatttgtta tttttccaagt gtgcatattg tacacttttt tggggatatg cttagtaatg     1920
ctacgtgtga ttttttctgga ggttgataac tttgcttgca gtagattttc tttaaaagaa     1980
tgggcagtta catgcatact tcaaaagtat tttcctgtaa aaaaaaaaa agttatatag      2040 gttttgtttg ctatcttaat tttggttgta ttctttgatg ttaacacatt ttgtataatt     2100
gtatcgtata gctgtattga atcatgtagt atcaaatatt gatgtgatt taatagtgtt     2160 aatcaattta aacccatttt agtcacttt ttttccaaa aaatactgc cagatgctga      2220 tgttcagtgt aatttctttg cctgttcagt tacagaaagt ggtgctcagt tgtagaatgt     2280
attgtacctt ttaacacctg atgtgtacat cccatgtaac agaaagggca acaataaaat     2340
agcaatccta aag                                                        2353
```

<210> SEQ ID NO 2
<211> LENGTH: 414
<212> TYPE: PRT
<213> ORGANISM: Homo sapiens

<400> SEQUENCE: 2

Met Ala Ser Gly Asp Thr Leu Tyr Ile Ala Thr Asp Gly Ser Glu Met
1               5                   10                  15

Pro Ala Glu Ile Val Glu Leu His Glu Ile Glu Val Glu Thr Ile Pro
            20                  25                  30

```
Val Glu Thr Ile Glu Thr Thr Val Gly Glu Glu Glu Glu Asp
        35              40                  45

Asp Asp Asp Glu Asp Gly Gly Gly Asp His Gly Gly Gly Gly
    50              55              60

His Gly His Ala Gly His His His His His His His His His
65              70                  75                  80

Pro Pro Met Ile Ala Leu Gln Pro Leu Val Thr Asp Pro Thr Gln
                85              90                  95

Val His His His Gln Glu Val Ile Leu Val Gln Thr Arg Glu Glu Val
            100             105                 110

Val Gly Gly Asp Asp Ser Asp Gly Leu Arg Ala Glu Asp Gly Phe Glu
            115             120                 125

Asp Gln Ile Leu Ile Pro Val Pro Ala Pro Ala Gly Gly Asp Asp Asp
        130             135             140

Tyr Ile Glu Gln Thr Leu Val Thr Val Ala Ala Ala Gly Lys Ser Gly
145             150             155                 160

Gly Gly Gly Ser Ser Ser Ser Gly Gly Gly Arg Val Lys Lys Gly Gly
                165             170                 175

Gly Lys Lys Ser Gly Lys Lys Ser Tyr Leu Ser Gly Gly Ala Gly Ala
            180             185                 190

Ala Gly Gly Arg Gly Ala Asp Pro Gly Asn Lys Lys Trp Glu Gln Lys
        195             200                 205

Gln Val Gln Ile Lys Thr Leu Glu Gly Glu Phe Ser Val Thr Met Trp
    210             215                 220

Ser Ser Asp Glu Lys Lys Asp Ile Asp His Glu Thr Val Val Glu Glu
225             230             235                 240

Gln Ile Ile Gly Glu Asn Ser Pro Pro Asp Tyr Ser Glu Tyr Met Thr
                245             250                 255

Gly Lys Lys Leu Pro Pro Gly Gly Ile Pro Gly Ile Asp Leu Ser Asp
            260             265                 270

Pro Lys Gln Leu Ala Glu Phe Ala Arg Met Lys Pro Arg Lys Ile Lys
    275             280                 285

Glu Asp Asp Ala Pro Arg Thr Ile Ala Cys Pro His Lys Gly Cys Thr
290             295                 300

Lys Met Phe Arg Asp Asn Ser Ala Met Arg Lys His Leu His Thr His
305             310                 315                 320

Gly Pro Arg Val His Val Cys Ala Glu Cys Gly Lys Ala Phe Val Glu
            325             330                 335

Ser Ser Lys Leu Lys Arg His Gln Leu Val His Thr Gly Glu Lys Pro
            340             345                 350

Phe Gln Cys Thr Phe Glu Gly Cys Gly Lys Arg Phe Ser Leu Asp Phe
    355             360                 365

Asn Leu Arg Thr His Val Arg Ile His Thr Gly Asp Arg Pro Tyr Val
    370             375                 380

Cys Pro Phe Asp Gly Cys Asn Lys Lys Phe Ala Gln Ser Thr Asn Leu
385             390             395                 400

Lys Ser His Ile Leu Thr His Ala Lys Ala Lys Asn Asn Gln
            405             410
```

<210> SEQ ID NO 3
<211> LENGTH: 25
<212> TYPE: DNA
<213> ORGANISM: Artificial sequence
<220> FEATURE:
<223> OTHER INFORMATION: PCR primer -continued

```
<400> SEQUENCE: 3
gaaaacatct gcacacccac ggtcc                                              25

<210> SEQ ID NO 4
<211> LENGTH: 21
<212> TYPE: DNA
<213> ORGANISM: Artificial sequence
<220> FEATURE:
<223> OTHER INFORMATION: PCR primer

<400> SEQUENCE: 4
gtcctcctgt tgggaccaca c                                                  21

<210> SEQ ID NO 5
<211> LENGTH: 20
<212> TYPE: DNA
<213> ORGANISM: Artificial sequence
<220> FEATURE:
<223> OTHER INFORMATION: PCR primer

<400> SEQUENCE: 5
accacagtcc atgccatcac                                                    20

<210> SEQ ID NO 6
<211> LENGTH: 20
<212> TYPE: DNA
<213> ORGANISM: Artificial sequence
<220> FEATURE:
<223> OTHER INFORMATION: PCR primer

<400> SEQUENCE: 6
tccaccaccc tgttgctgta                                                    20
```

INHIBITING CELLULAR PROLIFERATION BY EXPRESSING YIN YANG-1

CROSS REFERENCE TO RELATED APPLICATIONS

This application claims the benefit of priority under 35 USC § 119(a)-(d) of International Application No. PCT/AU02/00629, with an international filing date of May 21, 2002, which claims priority to Australian Application No. PR 5185, filed May 22, 2001, which is incorporated herein by reference in its entirety.

BACKGROUND OF THE INVENTION

YY1 (yin-yang 1, also called NF-E1, delta, or UCRBP) is a GLI-Kruppel-type zinc finger nuclear factor that is able to repress, activate and initiate transcription depending on promoter architecture and the cellular environment (1). YY1 can activate or repress the c-fos promoter depending on the orientation of a YY1 recognition element in the promoter. YY1 can switch between an activator or repressor of the human papillomavirus type 18 promoter depending on the integrity of a distinct element upstream in the promoter (2). YY1 competes with NF-kappaB for overlapping binding sites in the serum amyloid A1 promoter and inhibits promoter activity by passive means. Similarly YY1 can antagonize the interaction of SRF to overlapping binding sites in the actin promoter. The four GLI-Kruppel-related zinc fingers at the carboxyl terminus of YY1 constitute a strong repression domain (3). YY1 functionally interacts with a large number of other key transcriptional regulators, such as Sp1, c-Myc, adenovirus E1A, the cAMP response element-binding protein-related factor, p300, and components of the general transcriptional apparatus including the large subunit of RNA polymerase II and transcription factor IIB (TFIIB) (4,5). The capacity of YY1 to bend DNA when it binds the promoter facilitates direct contact between regulatory proteins. YY1 can interact with histone deacetylases to repress the activity of certain promoters, including the human immunodeficiency virus type 1 long terminal repeat (6), thereby modulating histone and chromatin structure.

The pathogenesis of common vascular disorders such as atherosclerosis and restenosis after balloon angioplasty is believed to be mediated at least in part by phenotypic changes involving smooth muscle cells of the artery wall. These cells normally adopt a "contractile" phenotype (7) in the vessel wall, but upon activation (such as mechanical injury imparted by angioplasty balloons), these cells become "synthetic" (7) and contribute to developing lesions by migrating, proliferating, producing extracellular matrix, and elaborating and responding to a myriad of growth-regulatory molecules (8). YY1 can repress the promoters of a wide spectrum of pro-atherogenic genes, including cytokines, hormones and growth factors (9-14). As such, YY1 may play an atheroprotective role in the artery wall. However, whether YY1 is even expressed in the artery wall or is regulated in the adaptive response to injury is presently not known, nor is whether YY1 can influence the growth of smooth muscle cells or other cell types.

SUMMARY OF THE INVENTION

The present inventors have found that YY1 has an anti-proliferative activity.

Accordingly, in a first aspect the present invention consists in a method of preventing or reducing cellular proliferation, the method comprising administering to cells a composition which increases the level of YY1 protein in the cells.

In a preferred embodiment the composition increases the level of YY1 mRNA in the cells.

In a further preferred embodiment of the present invention the composition comprises nucleic acid encoding YY1, preferably DNA encoding YY1. It is also preferred that the DNA encoding YY1 is operatively linked to control sequences which promote expression of the DNA encoding YY1 in the cells.

In yet a further preferred embodiment the composition comprises a vector which comprises nucleic acid encoding YY1.

It is preferred that the cellular proliferation to be prevented or reduced is in cells other than HMEC-1 or bovine aortic endothelial cells or microvascular endothelial cells.

Clearly as the method of the present invention prevents or reduce cellular proliferation the method can be used in the treatment of disease states involving cellular proliferation. Such diseases include cancer, restenosis and atherosclerosis.

Following the findings of the present inventors that YY1 is a negative regulator of cellular proliferation the present invention also provides a method of screening for agents which reduce or prevent cellular proliferation.

Accordingly, in a second aspect the present invention consists in a method of screening for compounds which inhibit the proliferation of cells, the method comprising determining the ability of a putative compound to increase induction of YY1, increase expression of YY1 or increase the nuclear accumulation or activity of the YY1 gene product.

DETAILED DESCRIPTION OF THE INVENTION

Figure 1:
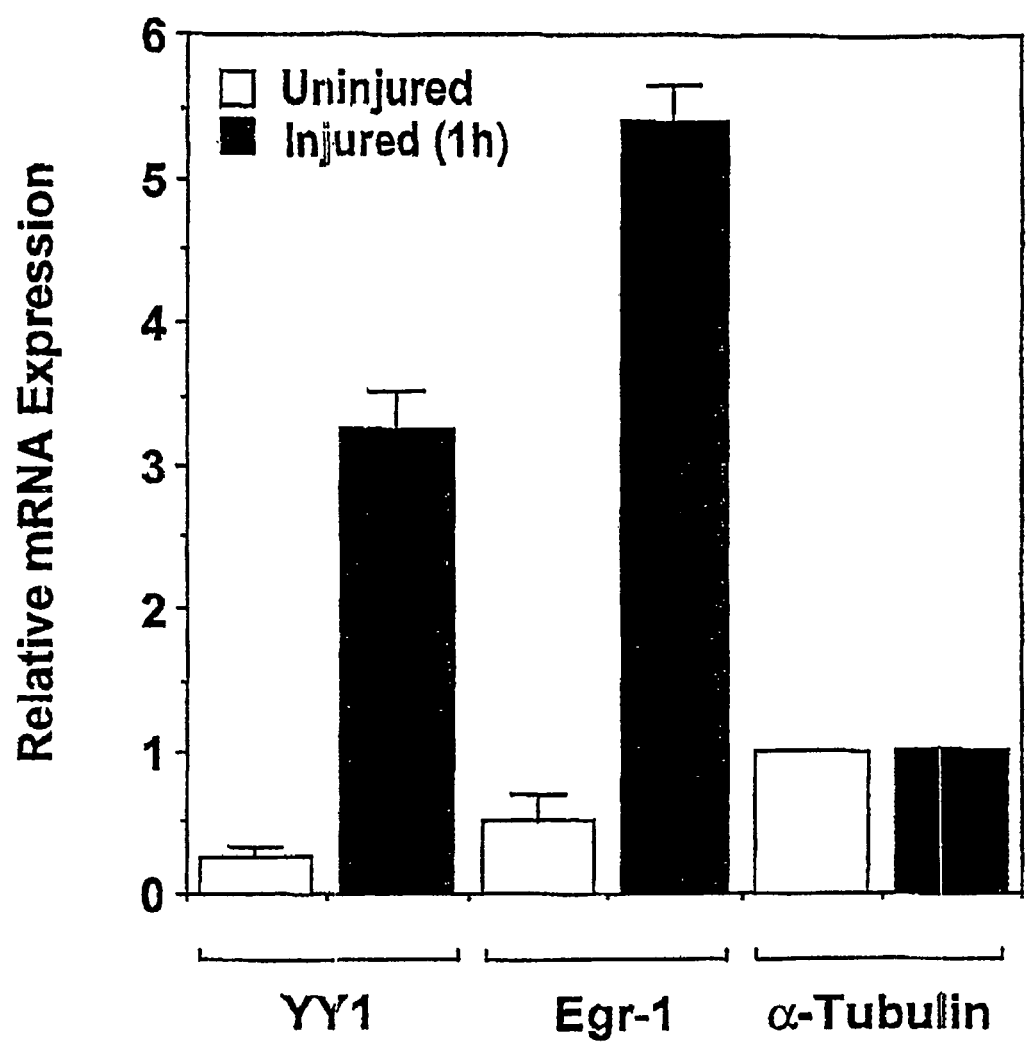
FIG. 1. YY1 is inducibly expressed in growth-quiescent vascular smooth muscle cells following mechanical injury. Growth-arrested smooth muscle cells were injured by scraping repeatedly with a sterile stainless steel comb, or left undisturbed, and total RNA was isolated after 1 h. Reverse-transcribed $^{32}$P-labeled cDNA was hybridized to cDNA array filters (Clontech) prior to washing, vacuum drying and quantitation of signal intensity by phosphorolmager analysis (ImageQuant, Molecular Dynamics). Data was normalized to levels of alpha-tubulin signal between injured and uninjured samples.

As mentioned above the inventors have determined that YY1 has anti-proliferative activity.

Accordingly, in a first aspect the present invention consists in a method of preventing or reducing cellular proliferation, the method comprising administering to cells a composition which increases the level of YY1 protein in the cells.

It is preferred that the composition increases the level of YY1 mRNA in the cells.

It is also preferred that the method is conducted in vivo.

In a preferred embodiment of the present invention the composition comprises nucleic acid encoding YY1, preferably DNA encoding YY1. It is also preferred that the DNA encoding YY1 is operatively linked to control sequences which promote expression of the DNA encoding YY1 in the cells.

Control sequences operably linked to sequences encoding YY1 include promoters/enhancers and other expression regulation signals. These control sequences may be selected to be compatible with cell in which expression of the sequence encoding YY1 is desired. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may also be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of alpha-actin, beta-actin, tubulin) or, alternatively, a tissue-specific manner (such as promoters of the genes for pyruvate kinase).

Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the sequence encoding YY1 can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

As will be recognised by those skilled in the art there are a number of situations in which reduction or prevention of cellular proliferation is desirable. These include restenosis following balloon angioplasty and cancer. In particular the use of gene therapy to inhibit restenosis following balloon angioplasty is attracting increasing interest (see Hiltunen et al, Vasc Med. 2000; 5 (1):41-8, Dedieu et al, Curr Cardiol Rep. 2000 January; 2 (1):39-47, Yla-Herttuala et al, Lancet. 2000 Jan. 15; 355 (9199):213-22, Laitinen et al, Curr Opin Lipidol. 1998 October; 9 (5):465-9, and O'Brien et al, Mayo Clin Proc 2000 August; 75 (8):831-4).

Administration of the composition may be effected or performed using any of the various methods and delivery systems known to those skilled in the art. The administering can be performed, for example, intravenously, orally, via implant, transmucosally, transdermally, topically, intramuscularly, subcutaneously or extracorporeally. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

It is currently preferred that the route of administration is topical. Topical delivery systems include, for example, gels and solutions, and can contain excipients such as solubilizers, permeation enhancers (e.g., fatty acids, fatty acid esters, fatty alcohols and amino adds), and hydrophilic polymers (e.g., polycarbophil and polyvinylpyrolidone). In the preferred embodiment, the pharmaceutically acceptable carrier is a liposome or a biodegradable polymer. Examples of carriers which can be used in this invention include the following: (1) Fugene6® (Roche); (2) SUPERFECT®(Qiagen); (3) Lipofectamine 2000®(GIBCO BRL); (4) CellFectin, 1:1.5 (M/M) liposome formulation of the cationic lipid N,NI,NII,NIII-tetramethyl-N,NI,NII,NIII-tetrapalmitylspermine and dioleoyl phosphatidyl-ethanolamine (DOPE)(GIBCO BRL); (5) Cytofectin GSV, 2:1 (M/M) liposome formulation of a cationic lipid and DOPE (Glen Research); (6) DOTAP (N-[1-(2, 3-dioleoyloxy)-N,N,N-trimethyl-ammoniummethylsulfate) (Boehringer Mannheim); and (7) Lipofectamine, 3:1 (M/M) liposome formulation of the polycationic lipid DOSPA and the neutral lipid DOPE (GIBCO BRL).

Transdermal delivery systems include patches, gels, tapes and creams, and can contain excipients such as solubilizers, permeation enhancers (e.g., fatty acids, fatty acid esters, fatty alcohols and amino acids), hydrophilic polymers (e.g., polycarbophil and polyvinylpyrolidone), and adhesives and tackifiers (e.g., polyisobutylenes, silicone-based adhesives, acrylates and polybutene).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc). Solutions, suspensions and powders for reconstitutable delivery systems include vehicles such as suspending agents (e.g., gums, xanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Delivery of the nucleic acid agents described may also be achieved via one or more, of the following non-limiting examples of vehicles:

(a) liposomes and liposome-protein conjugates and mixtures;

(b) non-liposomal lipid and cationic lipid formulations;

(c) activated dendrimer formulations;

(d) within a polymer formulation such as polyethylenimine (PEI) or pluronic gels or within ethylene vinyl acetate copolymer (EVAc). The polymer is preferably delivered intra-luninally;

(e) within a viral-liposome complex, such as Sendai virus;

(f) as a peptide-DNA conjugate;

(g) using catheters to deliver intra-luminal formulations of the nucleic acid as a solution or in a complex with a liposome;

(h) catheter delivery to adventitial tissue as a solution or in a complex with a liposome;

(i) the nucleic acid may be bound to a delivery agent such as a targeting moiety, or any suitable carrier such as a peptide or fatty acid molecule;

(j) the nucleic acid may be delivered by a double angioplasty balloon device fixed to catheter; or (k) the nucleic acid could be delivered on a specially prepared stent of the Schatz-Palmaz or derivative type. The stent may be coated with a polymer or agent impregnated with nucleic acid that allows controlled release of the molecules at the vessel wall.

While the majority of the above discussion focuses on the delivery of nucleic it will be understood that a similar effect can be achieved by exposing the cells to YY1 protein. Methods of delivery of proteins to cells are well known in the art.

Determining the prophylactically effective dose of the instant pharmaceutical composition can be done based on animal data using routine computational methods.

In the case of the prevention or reduction of cellular proliferation in cancer, in a preferred embodiment, the agent is injected into or proximal the tumour. Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

In a further aspect the present invention consists in an angioplastic stent for inhibiting onset of restenosis comprising an angioplastic stent operably coated with a prophylactically effective dose of an agent which increases the level of YY1 mRNA in cells.

It is preferred that the agent comprises nucleic acid encoding YY1, preferably DNA encoding YY1. It is also preferred that the DNA encoding YY1 is operatively linked to control sequences which promote expression of the DNA encoding YY1 in the cells.

In yet another aspect the present invention consists in a method for inhibiting the onset of restenosis in a subject undergoing angioplasty comprising topically administering a stent according to the present invention to the subject at around the time of angioplasty.

Angioplastic stents, also known by other terms such as "intravascular stents" or simple "stents", are well known in the art. They are routinely used to prevent vascular closure due to physical anomalies such as unwanted inward growth of vascular tissue due to surgical trauma. They often have a tubular, expanding lattice-type structure appropriate for their function, and can optionally be biodegradable.

In this invention, the stent can be operably coated with the instant pharmaceutical composition using any suitable means known in the art. Here, "operably coating" a stent means coating it in a way that permits the timely release of the pharmaceutical composition into the surrounding tissue to be treated once the coated stent is administered. Such coating methods, for example, can use the polymer polypyrrole.

As used herein, administration "at around the time of angioplasty" can be performed during the procedure, or immediately before or after the procedure. The administering can be performed according to known methods such as catheter delivery.

Tissue-specific promoters which are only active or have heightened activity in particular cells or tissues are particularly preferred. In the case of prevention or reduction of restenosis it is preferred to use a promoter specific for smooth muscle cells such as the SM 22 promoter (see Ribault et al, Circ Res. 2001; 88:468-475). In the case of cancer, for example prostate cancer, it is preferred to use a promoter active in the prostate such as the probasin promoter or the prostate specific antigen promoter. They may also be promoters that respond to specific stimuli, for example promoters that bind steroid hormone receptors.

In most instances where the method of the present invention is to be used in vivo in order to obtain good levels of expression of the sequence encoding YY1 it is preferred that the composition comprises a vector which comprises the nucleic acid encoding YY1. In particular it is preferred that the vector is a viral vector, a range of which are well known in the art. Particularly preferred viral vectors include retroviruses, lentiviruses, adenoviruses, hybrid vectors and herpes simplex type viruses.

Retroviral vectors of the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively).

Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

The lentivirus group can be split even further into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue.

Each retroviral genome comprises genes called gag, pol and env which code for virion proteins and enzymes. In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

The basic molecular organisation of an infectious retroviral RNA genome is (5') R-U5-gag, pol, env-U3-R (3'). In a defective retroviral vector genome gag, pol and env may be absent or not functional. The R regions at both ends of the RNA are repeated sequences. U5 and U3 represent unique sequences at the 5' and 3' ends of the RNA genome respectively.

Host range and tissue tropism varies between different retroviruses. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse. This transporter is ubiquitous and so these viruses are capable of infecting many cell types.

In some cases however, it may be beneficial, especially from a safety point of view, to target specifically restricted cells. Replacement of the env gene with a heterologous env gene is an example of a technique or strategy used to target specifically certain cell types. This technique is called pseudotyping and examples may be found in WO-A-98/05759, WO-A-98/05754, WO-A-97/17457, WO-A-96/09400 and WO-A-91/00047.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV in use typically carries non-viral coding sequences which are to be delivered by the vector to the target cell. An RRV is incapable of independent replication to produce infectious retroviral particles within the final target cell.

In a typical recombinant retroviral vector for use in gene therapy, at least part of one or more of the gag, pol and envprotein coding regions essential for replication may be removed from the virus. This makes the retroviral vector replication-defective. The removed portions may even be replaced by an NOI to generate a virus capable of integrating its genome into a host genome but wherein the modified viral genome is unable to propagate itself due to a lack of structural proteins. When integrated in the host genome, expression of the NOI occurs—resulting in, for example, a therapeutic and/or a diagnostic effect. Thus, the transfer of an NOI into a site of interest is typically achieved by: integrating the NOI into the recombinant viral vector; packaging the modified viral vector into a virion coat; and allowing transduction of a site of interest—such as a targeted cell or a targeted cell population.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pol and env genes. The packaging cell line produces the proteins required for packaging retroviral DNA but it cannot bring about encapsidation due to the lack of a psi region. However, when a recombinant vector carrying an NOI and a psi region is introduced into the packaging cell line, the helper proteins can package the psi-positive recombinant vector to produce the recombinant virus stock. This virus stock can be used to transduce cells to introduce the NOI into the genome of the target cells. It is preferred to use a psi packaging signal, called psi plus, that contains additional sequences spanning from upstream of the splice donor to downstream of the gag start codon (Bender et al., 1987) since this has been shown to increase viral titres.

The recombinant virus whose genome lacks all genes required to make viral proteins can transduce only once and cannot propagate. These viral vectors which are only capable of a single round of transduction of target cells are known as replication defective vectors. Hence, the NOI is introduced into the host/target cell genome without the generation of potentially harmful retrovirus. A summary of the available packaging lines is presented in Coffin et al., 1997 (ibid).

Retroviral packaging cell lines in which the gag, pol and envviral coding regions are carried on separate expression plasmids that are independently transfected into a packaging cell line are preferably used. This strategy, sometimes referred to as the three plasmid transfection method (Soneoka et al., 1995, Nucl. Acids Res. 23: 628-633), reduces the potential for production of a replication-competent virus since three recombinant events are required for wild type viral production. As recombination is greatly facilitated by homology, reducing or eliminating homology between the genomes of the vector and the helper can also be used to reduce the problem of replication-competent helper virus production.

An alternative to stably transfected packaging cell lines is to use transient transfected cell lines. Transient transfections may advantageously be used to measure levels of vector production when vectors are being developed. In this regard, transient transfection avoids the longer time required to generate stable vector-producing cell lines and may also be used if the vector or retroviral packaging components are toxic to cells. Components typically used to generate retroviral vectors include a plasmid encoding the gag/pol proteins, a plasmid encoding the env protein and a plasmid containing an NOI. Vector production involves transient transfection of one or more of these components into cells containing the other required components. If the vector encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient transfection that produce vector titre levels that are comparable to the levels obtained from stable vector-producing cell lines (Pear et al., 1993, PNAS 90: 8392-8396).

It is highly desirable to use high-titre virus preparations in both experimental and practical applications. Techniques for increasing viral titre include using a psi plus packaging signal as discussed above and concentration of viral stocks. In addition, the use of different envelope proteins, such as the G protein from vesicular-stomatitis virus has improved titres following concentration to $10^9$ per ml (Cosset et al., 1995, J. Virol. 69: 7430-7436). Another technique is the split intron system for constructing retroviral vectors—see PCT/GB98/02885.

In addition to manipulating the retroviral vector with a view to increasing vector titre, retroviral vectors have also been designed to induce the production of a specific NOI in transduced cells. As already mentioned, the most common retroviral vector design involves the replacement of retroviral sequences with one or more NOIs to create replication-defective vectors. With regard to regulation of expression of the NOI, there are three main approaches currently in use.

1. The simplest approach has been to use the promoter in the retroviral 5' LTR to control the expression of a cDNA encoding an NOI or to alter the enhancer/promoter of the LTR to provide tissue-specific expression or inducibility. Where multiple NOIs are inserted, the additional downstream NOIs can be expressed from a polycistronic mRNA by the use of internal ribosome entry sites.

2. The NOI may be operably linked to an internal heterologous promoter. This arrangement permits more flexibility in promoter selection. Additional NOIs can still be expressed from the 5'LTR or the LTR can be mutated to prevent expression following infection of a target cell.

3. The NOI is inserted together with regulatory control elements in the reverse orientation to the 5'LTR. Genomic sequences including enhancers, promoters, introns and 3'regions may be included. In this way it may be possible to achieve tightly regulated tissue-specific gene expression.

The NOI may or may not include a selectable marker. If the vector contains an NOI that is not a selectable marker, the vector can be introduced into packaging cells by co-transfection with a selectable marker present on a separate plasmid. This strategy has an appealing advantage for gene therapy in that a single protein is expressed in the ultimate target cells and possible toxicity or antigenicity of a selectable marker is avoided. However, when the inserted gene is not selectable, this approach has the disadvantage that it is more difficult to generate cells that produce a high titre vector stock. In addition it is usually more difficult to determine the titre of the vector.

The current methodologies used to design retroviral vectors that express two or more proteins have relied on three general strategies. These include: (i) the expression of different proteins from alternatively spliced mRNAs transcribed from one promoter; (ii) the use of the promoter in the 5' LTR and internal promoters to drive transcription of different cDNAs and (iii) the use of internal ribosomal entry site (IRES) elements to allow translation of multiple coding regions from either a single mRNA or from fusion proteins that can then be expressed from an open reading frame.

Vectors containing internal heterologous promoters have been widely used to express multiple genes. An internal promoter makes it possible to exploit promoter/enhancer combinations other than the viral LTR for driving gene expression. Multiple internal promoters can be included in a retroviral vector and it has proved possible to express at least three different cDNAs each from its own promoter.

Lentiviruses

The lentivirus group can be into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue. Thus, lentiviral vectors may advantageously be used in the present invention since lentiviruses are capable of infecting a wide range of non-dividing cells, by contrast to certain other retroviruses that require cell division for stable integration.

A number of vectors have been developed based on various members of the lentivirus sub-family of the retroviridae and a number of these are the subject of patent applications (WO-A-98/18815; WO-A-97/12622). Preferred lentiviral vectors are based on HIV, SIV or EIAV. The simplest vectors constructed from HIV-1 have the complete HIV genome except for a deletion of part of the env coding region or replacement of the nefcoding region. Notably these vectors express gag/pol and all of the accessory genes hence require only an envelope to produce infectious virus partides. Of the accessory genes vif, vpr, vpu and nef are non-essential. More recently however vectors have been described that are efficient yet lack most or all of the accessory factors, for example Blomer et al., 1997 and Kim et al., 1998. Thus a lentiviral vector of the invention preferably lacks at least one accessory gene, more preferably all accessory genes.

One preferred general format for HIV-based lentiviral vectors is, HIV 5'LTR and leader, some gag coding region sequences (to supply packaging functions), a reporter cassette, the rev response element (RRE) and the 3'LTR. In these vectors gag/pol, accessory gene products and envelope functions are supplied either from a single plasmid or from two or more co-transfected plasmids, or by co-infection of vector containing cells with HIV. More recently the lentiviral vector configurations have been further refined. For example self inactivating HIV vectors have been produced where the HIV LTR is deleted to restrict expression to the internal cassette (Myoshi et al., 1998).

In a preferred embodiment, the lentiviral vector of the present invention is a non-primate lentiviral vector, for example EIAV. We have shown recently (U.K. patent application nos. 9811037.2 and 9727135.7) that the amount of vector genomic sequence required from a non-primate lentivirus to produce an efficient cloning vector is substantially less than has been described for an HIV vector. We have shown that a minimal EIAV vector lacking large regions of the gag gene suffices for efficient packaging and indeed leads to higher viral titres. Thus, a minimal EIAV genome vector typically comprises a promoter and optionally an enhancer capable of directing expression of a retroviral vector genome comprising, in order, the following elements from an EIAV: part of the 5'LTR containing an R-region and a U5 region; sequences from the 5' untranslated region of the gag gene containing a functional packaging signal and a portion of the gag coding sequence; an insertion site for a gene of interest and a 3'LTR from EIAV. The 3'LTR may be a hybrid LTR containing at least the polypurine tract and R-U5 region from an EIAV and sequences from another source to replace all or part of the U3 region. Alternatively, the R region in the 5'and 3'LTRs may be replaced. WO-A-96/33623 describes a method for replacing both the U3 and R regions of retroviral vector genomes.

Preferably, the portion of the gag gene contains less than the first 350 nucleotides of the gag coding region, more preferably only the first 150 or 109 nucleotides of the gag coding region, only about the first 109 nucleotides being especially preferred.

In a particularly preferred embodiment of the first aspect of the invention, a hCMV-MIE promoter enhancer is used to direct expression of the retroviral RNA transcript. The U3 region enhancer may, for example, be replaced by a hypoxia responsive enhancer (HRE) of the present invention and an SV40 or MLV promoter.

The minimal EIAV vector also lacks S2, Tat, Rev and dUTPase genes but may still be used in vector production or for transduction of dividing and non-dividing cells. The viral genome may typically be packaged in cells by providing gagpol and env functions in trans. For example DNA sequences encoding gagpol and env may be co-introduced into a cell along with the minimal vector as described above for retroviruses in general. Preferably the gagpol sequence is of non-primate lentiviral origin. It is particularly advantageous to include the leader sequences between the end of the 5' LTR and the ATG start codon of gag upstream of the gagpol coding sequence to provide for maximum gagpol expression. It may also be desirable to include the Rev and/or RRE sequences although this is not essential and may be eliminated by codon optimisation of the EIAV gagpol.

Adenoviruses

The adenovirus is a double-stranded, linear DNA virus that does not go through an RNA intermediate. There are over 50 different human serotypes of adenovirus divided into 6 subgroups based on the genetic sequence homology all of which exhibit comparable genetic organisation. Human adenovirus group C serotypes 2 and 5 (with 95% sequence homology) are most commonly used in adenoviral vector systems and are normally associated with upper respiratory tract infections in the young.

The adenoviruses/adenoviral vectors of the invention may be of human or animal origin. As regards the adenoviruses of human origin, preferred adenoviruses are those classified in group C, in particular the adenoviruses of type 2 (Ad2), 5 (Ad5), 7 (Ad7) or 12 (Ad12). More preferably, it is an Ad2 or Ad5 adenovirus. Among the various adenoviruses of animal origin, canine adenovirus, mouse adenovirus or an avian adenovirus such as CELO virus (Cotton et al., 1993, J Virol 67:3777-3785) may be used. With respect to animal adenoviruses it is preferred to use adenoviruses of canine or ovine origin, and especially the strains of the CAV2 adenoviruses [manhattan strain or A26/61 (ATCC VR-800) for example] and the ovine adenoviruses of WO 96/03508. Other adenoviruses of animal origin include those cited in application WO-A-94/26914 incorporated herein by reference.

As mentioned above, the organisation of the adenovirus genome is similar in all of the adenovirus groups and specific functions are generally positioned at identical locations for each serotype studied. The genome of adenoviruses comprises an inverted terminal repeat (ITR) at each end, an encapsidation sequence (Psi), early genes and late genes. The main early genes have been classified into an array of intermediate early (E1a), delayed early (E1b, E2a, E2b, E3 and E4), and intermediate regions. Among these, the genes contained in the E1 region in particular are necessary for viral propagation. The main late genes are contained in the L1 to L5 regions. The genome of the Ad5 adenovirus has been completely sequenced and is available on a database (see particularly Genbank Accession No. M73260). Likewise, parts, or even all of other adenoviral genomes (such as Ad2, Ad7, Ad12) have also been sequenced.

For use as recombinant vectors, an adenovirus is typically modified so as to make it incapable of replicating in an infected cell.

Thus, constructs described in the prior art include adenoviruses deleted for the E1 region, essential for viral replication, into which are inserted the heterologous DNA sequences (Levrero et al., 1991, Gene 101: 195; Gosh-Choudhury et al., 1986, Gene 50: 161). Moreover, to improve the properties of the vector, it has been proposed to create other deletions or modifications in the adenovirus genome. Thus, a heat-sensitive point mutation has been introduced into the ts125 mutant, making it possible to inactivate the 72 kDa DNA-binding protein (DBP). Preferably, a recombinant adenoviral vector used in the invention comprises a deletion in the E1 region of its genome. More particularly, it comprises a deletion in the E1a and E1b regions. According to a particularly preferred mode, the E1 region is inactivated by deletion of a PvuII-BglII fragment stretching from nudeotide 454 to nudeotide 3328, in the Ad5 adenovirus sequence (Genbank Accession No. M73260). In another preferred embodiment, the E1 region is inactivated by deletion of an HinfII-Sau3A fragment stretching from nudeotide 382 to nudeotide 3446.

Other adenoviral vectors comprise a deletion of another region essential for viral replication and/or propagation, the E4 region. The E4 region is involved in the regulation of the expression of the late genes, in the stability of the late nuclear RNAs, in decreasing host cell protein expression and in the efficiency of the replication of the viral DNA. Adenoviral vectors in which the E1 and E4 regions are deleted therefore possess very reduced viral gene expression and transcriptional background noise. Such vectors have been described for example in applications WO-A-94/28152, WO-A-95/02697, WO-A-96/22378. In addition, vectors carrying a modification of the IVa2 gene have also been described (WO-A-96/10088).

According to a preferred variant, a recombinant adenoviral vector used in the invention comprises, in addition, a deletion in the E4 region of its genome. More particularly, the deletion in the E4 region affects all the open reading frames. There may be mentioned, by way of a precise example, deletions of nucleotides 33466-35535 or 33093-35535. In particular, preferred vectors comprise a deletion of the whole of the E4 region. This may be carried deletion or excision of an MaeII-MscI fragment corresponding to nucleotides 35835-32720. Other types of deletions in the E4 region are described in applications WO-A-95/02697 and WO-A-96/22378, incorporated herein by reference.

Alternatively, only a functional part of E4 is deleted. This part comprises at least the ORF3 and ORF6 frames. By way of example, these coding frames can be deleted from the genome in the form of PvuII-AluI and Bgl-PvuII fragments respectively, corresponding to nucleotides 34801-34329 and 34115-33126 respectively. The deletions of the E4 region of the virus Ad2 dl808 or of viruses Ad5 dl1004, Ad5 dl1007, Ad5 dl1011 or Ad5 dl1014 can also be used within the framework of the invention.

The positions given above refer to the wild-type Ad5 adenovirus sequence as published and accessible on a database. Although minor variations may exist between the various adenovirus serotypes, these positions are generally applicable to the construction of recombinant adenoviruses according to the invention from any serotype, and especially the adenoviruses Ad2 and Ad7.

Moreover, the adenoviruses produced may possess other alterations in their genome. In particular, other regions may be deleted to increase the capacity of the virus and reduce its side effects linked to the expression of viral genes. Thus, all or part of the E3 or IVa2 region in particular may be deleted. As regards the E3 region, it may however be particularly preferred to conserve the part encoding the gp19K protein. This protein indeed makes it possible to prevent the adenoviral vector from becoming the subject of an immune reaction which (i) would limit its action and (ii) could have undesirable side effects. According to a specific mode, the E3 region is deleted and the sequence encoding the gp19K protein is reintroduced under the control of a heterologous promoter.

The sequence encoding YY1/NOI can be inserted into various sites of the recombinant genome. It can be inserted at into the E1, E3 or E4 region, as a replacement for the deleted or surplus sequences. It can also be inserted into any other site, outside the sequences necessary in cis for the production of the viruses (ITR sequences and encapsidation sequence).

The E2 region is essential as it encodes the 72 kDa DNA binding protein, DNA polymerase and the 80 kDa precursor of the 55 kDa Terminal Protein (TP) needed for protein priming to initiate DNA synthesis.

An alternative approach to making a more defective virus has been to "gut" the virus completely maintaining only the terminal repeats required for viral replication. The "gutted" or "gutless" viruses can be grown to high titres with a first generation helper virus in the 293 cell line.

The recombinant adenoviruses are typically produced in an encapsidation cell line, which is a cell line capable of complementing in trans one or more of the functions deficient in the recombinant adenoviral genome. One of these lines is for example line 293, into which part of the adenovirus genome has been integrated. More precisely, line 293 is a human kidney embryonic cell line containing the left end (about 11-12%) of the genome of serotype 5 adenovirus (Ad5), comprising the left ITR, the encapsidation region, the E1 region, including E1a and E1b, the region encoding protein pIX and part of the region encoding protein pIVa2. This line is capable of transcomplementing recombinant adenoviruses defective for the E1 region, that is to say lacking all or part of the E1 region, and of producing viral stocks having high titres. This line is also capable of producing, at a permissive temperature (32° C.), virus stocks comprising, in addition, the heat-sensitive E2 mutation.

Other cell lines capable of complementing the E1 region have been described, based in particular on human lung carcinoma cells A549 (WO 94/28152) or on human retinoblasts (Hum. Gen. Ther. (1996) 215). Moreover, cell lines capable of transcomplementing several adenovirus functions have also been described, for example cell lines complementing the E1 and E4 regions (Yeh et al., 1996, J. Virol. 70: 559; Krougliak et al., 1995, Hum. Gen. Ther. 6: 1575) and lines complementing the E1 and E2 regions (WO-A-94/28152, WO-A-95/02697, WO-A-95/27071).

The recombinant adenoviruses are usually produced by introducing the viral DNA into the encapsidation line, followed by lysis of the cells after about 2 or 3 days (the kinetics of the adenoviral cycle being 24 to 36 hours). For carrying out the process, the viral DNA introduced may be the complete recombinant viral genome, optionally constructed in a bacterium (WO-A-96/25506) or in a yeast (WO-A-95/03400), transfected into the cells. It may also be a recombinant virus used to infect the encapsidation line. The viral DNA may also be introduced in the form of fragments each carrying part of the recombinant viral genome and a region of homology which makes it possible, after introduction into the encapsidation cell, to reconstitute the recombinant viral genome by homologous recombination between the various fragments.

Replication-competent adenoviruses can also be used for gene therapy. For example, the E1a gene can be inserted into a first generation virus under the regulation of a tumour-specific promoter. In theory, following injection of the virus into a tumour, it could replicate specifically in the tumour but not in the surrounding normal cells.

Thus, given that the HRE construct of the present invention may be preferentially active in certain tumour tissue by virtue of the hypoxic conditions that exist within many solid tumour masses, the present invention provides an adenovirus vector comprising the sequence encoding YY1 operably linked to a nucleic acid sequence encoding an adenoviral E1a polypeptide. The E1a polypeptide under the control of the HRE enhancer would only be expressed under hypoxic conditions and therefore the adenovirus would only be replication competent under hypoxic conditions. The adenovirus lacks an endogenous E1 gene, and preferably also lacks an endogenous E3 gene. Other regions of the adenovirus genome which may be deleted are described above. It may also be desirable to include all or part of the E3 gene under the control of a hypoxia response element such that host cell immune modulation is balances to obtain the correct viral spread within the tumour and immune response to infected cells.

An adenovirus defective only for E1b has been used specifically for antitumour treatment in phase-1 clinical trials. The polypeptides encoded by E1b are able to block p53-mediated apoptosis, preventing the cell from killing itself in response to viral infection. Thus, in normal non tumour cells, in the absence of E1b, the virus is unable to block apoptosis and is thus unable to produce infectious virus and spread. In tumour cells deficient in p53, the E1b defective virus can grow and spread to adjacent p53-defective tumour cells but not to normal cells.

Consequently, it is preferred that the E1a-expressing adenoviruses of the present invention lack a functional E1b gene.

Other essential viral genes may also be placed under the control of a hypoxia responsive regulatory element.

Hybrid Vector Systems

Hybrid adenovirus/retrovirus systems may also be used whereby the features of adenoviruses are combined with the genetic stability of retroviruses. These hybrid viral vectors use the adenovirus to transduce target cells when then become transient retroviral producer cells that can stably infect neighbouring cells.

A hybrid viral vector system of the present invention comprises one or more primary viral vectors which encode a secondary viral vector, the primary vector or vectors being capable of infecting a first target cell and of expressing therein the secondary viral vector, which secondary vector is capable of transducing a secondary target cell.

Thus a genetic vector of the invention consists of a primary vector manufactured in vitro which encodes the genes necessary to produce a secondary vector in vivo. In use, the secondary vector carries one or more selected genes for insertion into the secondary target cell. The selected genes may be one or more marker genes and/or therapeutic genes (see above).

The primary viral vector or vectors may be a variety of different viral vectors, such as retroviral (including lentiviral), adenoviral, herpes virus or pox virus vectors, or in the case of multiple primary viral vectors, they may be a mixture of vectors of different viral origin. In whichever case, the primary viral vectors are preferably defective in that they are incapable of independent replication. Thus, they are capable of entering a target cell and delivering the secondary vector sequences, but not of replicating so as to go on to infect further target cells.

In the case where the hybrid viral vector system comprises more than one primary vector to encode the secondary vector, all of the primary vectors will be used to infect a primary target cell population, usually simultaneously. Preferably, there is a single primary viral vector which encodes all components of the secondary viral vector.

The preferred single or multiple primary viral vectors are adenoviral vectors. Adenovirus vectors have significant advantages over other viral vectors in terms of the titres which can be obtained from in vitro cultures. The adenoviral particles are also comparatively stable compared with those of enveloped viruses and are therefore more readily purified and stored.

The secondary viral vector is preferably a retroviral vector, more preferably a lentiviral vector. The construction of an adenolentiviral system is described in the Examples. The secondary vector is produced by expression of essential genes for assembly and packaging of a defective viral vector particle, within the primary target cells. It is defective in that it is incapable of independent replication. Thus, once the secondary retroviral vector has transduced a secondary target cell, it is incapable of spreading by replication to any further target cells.

The secondary vector may be produced from expression of essential genes for retroviral vector production encoded in the DNA of the primary vector. Such genes may include a gag-pol gene from a retrovirus, an envelope gene from an enveloped virus and a defective retroviral genome containing one or more therapeutic genes. The defective retroviral genome contains in general terms sequences to enable reverse transcription, at least part of a 5'long terminal repeat (LTR), at least part of a 3'LTR and a packaging signal.

Importantly, the secondary vector is also safe for in vivo use in that incorporated into it are one or more safety features which eliminate the possibility of recombination to produce an infectious virus capable of independent replication.

To ensure that it is replication defective the secondary vector may be encoded by a plurality of transcription units, which may be located in a single or in two or more adenoviral or other primary vectors. Thus, there may be a transcription unit encoding the secondary vector genome, a transcription unit encoding gag-pol and a transcription unit encoding env. Alternatively, two or more of these may be combined. For example, nucleic acid sequences encoding gag-pol and env, or env and the genome, may be combined in a single transcription unit. Ways of achieving this are known in the art.

Transcription units as described herein are regions of nucleic acid containing coding sequences and the signals for achieving expression of those coding sequences independently of any other coding sequences. Thus, each transcription unit generally comprises at least a promoter, an enhancer and a polyadenylation signal. The promoter and enhancer of the transcription units encoding the secondary vector are preferably strongly active, or capable of being strongly induced, in the primary target cells under conditions for production of the secondary viral vector. The promoter and/or enhancer may be constitutively efficient, or may be tissue or temporally restricted in their activity.

Safety features which may be incorporated into the hybrid viral vector system are described below. One or more such features may be present.

Firstly, sequence homology between the sequences encoding the components of the secondary vector may be avoided by deletion of regions of homology. Regions of homology allow genetic recombination to occur. In a particular embodiment, three transcription units are used to construct a secondary retroviral vector. A first transcription unit contains a retroviral gag-pol gene under the control of a non-retroviral promoter and enhancer. A second transcription unit contains a retroviral env gene under the control of a non-retroviral promoter and enhancer. A third transcription unit comprises a defective retroviral genome under the control of a non-retroviral promoter and enhancer. In the native retroviral genome, the packaging signal is located such that part of the gag sequence is required for proper functioning. Normally when retroviral vector systems are constructed therefore, the packaging signal, including part of the gag gene, remains in the vector genome. In the present case however, the defective retroviral genome contains a minimal packaging signal which does not contain sequences homologous to gag sequences in the first transcription unit. Also, in retroviruses, for example Moloney Murine Leukaemia virus (MMLV), there is a small region of overlap between the 3' end of the pol coding sequence and the 5' end of env. The corresponding region of homology between the first and second transcription units may be removed by altering the sequence of either the 3' end of the polcoding sequence or the 5' end of envso as to change the codon usage but not the amino acid sequence of the encoded proteins.

Secondly, the possibility of replication competent secondary viral vectors may be avoided by pseudotyping the genome of one retrovirus with the envelope protein of another retrovirus or another enveloped virus so that regions of homology between the env and gag-pol components are avoided. In a particular embodiment the retroviral vector is constructed from the following three components. The first transcription unit contains a retroviral gag-pol gene under the control of a non-retroviral promoter and enhancer. The second transcription unit contains the env gene from the alternative enveloped virus, under the control of a non-retroviral promoter and enhancer. The third transcription unit comprises a defective retroviral genome under the control of a non-retroviral promoter and enhancer. The defective retroviral genome contains a minimal packaging signal which does not contain sequences homologous to gag sequences in the first transcription unit.

Pseudotyping may involve for example a retroviral genome based on a lentivirus such as an HIV or equine infectious anaemia virus (EIAV) and the envelope protein may for example be the amphotropic envelope protein designated 4070A. Alternatively, the retroviral genome may be based on MMLV and the envelope protein may be a protein from another virus which can be produced in non-toxic amounts within the primary target cell such as an Influenza haemagglutinin or vesicular stomatitis virus G protein. In another alternative, the envelope protein may be a modified envelope protein such as a mutant or engineered envelope protein. Modifications may be made or selected to introduce targeting ability or to reduce toxicity or for another purpose.

Thirdly, the possibility of replication competent retroviruses can be eliminated by using two transcription units constructed in a particular way. The first transcription unit contains a gag-pol coding region under the control of a promoter-enhancer active in the primary target cell such as a hCMV promoter-enhancer or a tissue restricted promoter-enhancer. The second transcription unit encodes a retroviral genome RNA capable of being packaged into a retroviral particle. The second transcription unit contains retroviral sequences necessary for packaging, integration and reverse transcription and also contains sequences coding for an env protein of an enveloped virus and the coding sequence of one or more therapeutic genes.

In a preferred embodiment the hybrid viral vector system according to the invention comprises single or multiple adenoviral primary vectors which encodes or encode a retroviral secondary vector. Adenoviral vectors for use in the invention may be derived from a human adenovirus or an adenovirus which does not normally infect humans. Preferably the vectors are derived from Adenovirus Type 2 or adenovirus Type 5 (Ad2 or Ad5) or a mouse adenovirus or an avian adenovirus such as CELO virus. The vectors may be replication competent adenoviral vectors but are more preferably defective adenoviral vectors. Adenoviral vectors may be rendered defective by deletion of one or more components necessary for replication of the virus. Typically, each adenoviral vector contains at least a deletion in the E1 region. For production of infectious adenoviral vector particles, this deletion may be complemented by passage of the virus in a human embryo fibroblast cell line such as human 293 cell line, containing an integrated copy of the left portion of Ad5, including the E1 gene. The capacity for insertion of heterologous DNA into such vectors can be up to approximately 7 kb. Thus such vectors are useful for construction of a system according to the invention comprising three separate recombinant vectors each containing one of the essential transcription units for construction of the retroviral secondary vector.

Alternative adenoviral vectors are known in the art which contain further deletions in other adenoviral genes and these vectors are also suitable for use in the invention. Several of these second generation adenoviral vectors show reduced immunogenicity (eg E1+E2 deletions Gorziglia et al., 1996, J. Virol. 70: 4173-4178; E1+E4 deletions Yeh et al., 1996, J. Virol. 70: 559). Extended deletions serve to provide additional cloning capacity for the introduction of multiple genes in the vector. For example a 25 kb deletion has been described (Lieber et al., 1996, J. Virol. 70: 8944-8960) and a cloning vector deleted of all viral genes has been reported (Fisher et al., 1996, Virolology 217: 11-22) which will permit the introduction of more than 35 kb of heterologous DNA. Such vectors may be used to generate an adenoviral primary vector according to the invention encoding two or three transcription units for construction of the retroviral secondary vector.

Embodiments of the invention described solve one of the major problems associated with adenoviral and other viral vectors, namely that gene expression from such vectors is transient. The retroviral particles generated from the primary target cells can infect secondary target cells and gene expression in the secondary target cells is stably maintained because of the integration of the retroviral vector genome into the host cell genome. The secondary target cells do not express significant amounts of viral protein antigens and so are less immunogenic than the cells transduced with adenoviral vector.

The use of a retroviral vector as the secondary vector is also advantageous because it allows a degree of cellular discrimination, for instance by permitting the targeting of rapidly dividing cells. Furthermore, retroviral integration permits the stable expression of therapeutic genes in the target tissue, including stable expression in proliferating target cells.

Preferably, the primary viral vector preferentially infects a certain cell type or cell types. More preferably, the primary vector is a targeted vector, that is it has a tissue tropism which is altered compared to the native virus, so that the vector is targeted to particular cells. The term "targeted vector" is not necessarily linked to the term "target cell". "Target cell" simply refers to a cell which a vector, whether native or targeted, is capable of infecting or transdudng.

The secondary viral vectors may also be targeted vectors. For retroviral vectors, this may be achieved by modifying the envelope protein. The envelope protein of the retroviral secondary vector needs to be a non-toxic envelope or an envelope which may be produced in non-toxic amounts within the primary target cell, such as for example a MMLV amphotropic envelope or a modified amphotropic envelope. The safety feature in such a case is preferably the deletion of regions or sequence homology between retroviral components.

The secondary target cell population may be the same as the primary target cell population. For example delivery of a primary vector of the invention to tumour cells leads to replication and generation of further vector particles which can transduce further tumour cells. Alternatively, the secondary target cell population may be different from the primary target cell population. In this case the primary target cells serve as an endogenous factory within the body of the treated individual and produce additional vector particles which can infect the secondary target cell population. For example, the primary target cell population may be haematopoietic cells transduced by the primary vector in vivo or ex vivo. The primary target cells are then delivered to or migrate to a site within the body such as a tumour and produce the secondary vector particles, which are capable of transducing for example tumour cells within a solid tumour.

This permits the localised production of high titres of defective retroviral vector particles in vivo at or near the site at which action of a therapeutic protein or proteins is required with consequent efficient transduction of secondary target cells. This is more efficient than using either a defective adenoviral vector or a defective retroviral vector alone.

This also permits the production of retroviral vectors such as MMLV-based vectors in non-dividing and slowly-dividing cells in vivo. It had previously been possible to produce MMLV-based retroviral vectors only in rapidly dividing cells such as tissue culture-adapted cells proliferating in vitro or rapidly dividing tumour cells in vivo. Extending the range of cell types capable of producing retroviral vectors is advantageous for delivery of genes to the cells of solid tumours, many of which are dividing slowly, and for the use of non-dividing cells such as endothelial cells and cells of various haematopoietic lineages as endogenous factories for the production of therapeutic protein products.

Herpes Simplex Viruses

1. Viral Strains

The HSV vectors of the invention comprising a sequence encoding YY1 may be derived from, for example, HSV1 or HSV2 strains, or derivatives thereof, preferably HSV1. Derivatives include inter-type recombinants containing DNA from HSV1 and HSV2 strains. Derivatives preferably have at least 70% sequence homology to either the HSV1 or HSV2 genomes, more preferably at least 90%, even more preferably 95%.

The use of HSV strains in therapeutic procedures will require the strains to be attenuated so that they cannot establish a lytic cycle. In particular, if HSV vectors are to be used for gene therapy in humans the sequence encoding YY1 should preferably be inserted into an essential gene. This is because if a vector virus encounters a wild-type virus transfer of a heterologous gene to the wild-type virus could occur by recombination. However as long as the sequence encoding YY1 is inserted into an essential gene this recombinational transfer would also delete the essential gene in the recipient virus and prevent 'escape' of the heterologous gene into the replication competent wild-type virus population.

Attenuated strains may be used to produce the HSV strain of the present invention, here given as examples only, including strains that have mutations in either ICP34.5 or ICP27, for example strain 1716 (MacLean et al., 1991, J Gen Virol 72: 632-639), strains R3616 and R4009 (Chou and Roizman, 1992, PNAS 89: 3266-3270) and R930 (Chou et al., 1994, J. Virol 68: 8304-8311) all of which have mutations in ICP34.5, and d27-1 (Rice and Knipe, 1990, J. Virol 64: 1704-1715) which has a deletion in ICP27. Alternatively strains deleted for ICP4, ICP0, ICP22, ICP6, ICP47, vhs or gH, with an inactivating mutation in VMW65, or with any combination of the above may also be used to produce HSV strains of the invention.

The terminology used in describing the various HSV genes is as found in Coffin and Latchman, 1996. Herpes simplex virus-based vectors. In: Latchman DS (ed). Genetic manipulation of the nervous system. Academic Press: London, pp 99-114.

2. Complementing Cell Lines

HSV viruses defective in ICP27 are propagated in a cell line expressing ICP27, for example V27 cells (Rice and Knipe, 1990, J. Virol 64: 1704-1715) or 2-2 cells (Smith et al., 1992, Virology 186: 74-86). ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27 mutant HSV strains, using methods known to those skilled in the art (for example as described in Rice and Knipe, 1990).

Cell lines which do not allow reversion of an ICP27mutant HSV strain to a strain with functional ICP27 are produced as described above, ensuring that the vector comprising a functional ICP27 gene does not contain sequences that overlap with (i.e. are homologous to) sequences remaining in the ICP27mutant virus.

Where HSV strains of the invention comprise inactivating modifications in other essential genes, for example ICP4, complementing cell lines will further comprise a functional HSV gene which complements the modified essential gene in the same manner as described for ICP27.

3. Methods of Mutation

HSV genes may be rendered functionally inactive by several techniques well known in the art For example, they may be rendered functionally inactive by deletions, substitutions or insertions, preferably by deletion. Deletions may remove portions of the genes or the entire gene. Inserted sequences may include the expression cassette described above.

Mutations are made in the HSV strains by homologous recombination methods well-known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ for screening recombinant viruses by, for example, β-galactosidase activity.

Mutations may also be made in other HSV genes, for example genes such as ICP0, ICP4, ICP6, ICP22, ICP47, VMW65, gH or vhs. In the case of the VMW65 gene, the entire gene is not deleted since it encodes an essential structural protein, but a small inactivating insertion is made which abolishes the ability of VMW65 to transcriptionally activate IE genes (Ace et al., 1989, J Virol 63: 2260-2269).

4. HSV Strains Comprising a Sequence Encoding YY1

A sequence encoding YY1 may be inserted into the HSV genome at any location provided that the virus can still be propagated, which may require the use of a cell line carrying another HSV essential gene (as described in 2.) if the NOI is inserted into an essential gene. For example, if the sequence is inserted into the ICP27 gene of the HSV strain, then a cell-line expressing ICP27 would be needed. The sequence encoding YY1 is preferably inserted into the region of the ICP27 mutation as in the unlikely event that the mutation is repaired by recombination with a wild-type virus, the repair would remove the inserted sequence encoding YY1.

The sequence encoding YY1 may be inserted into the HSV genome by homologous recombination of HSV strains with, for example, plasmid vectors carrying the expression cassette flanked by HSV sequences, as described above for introducing mutations. The sequence encoding YY1 may be introduced into a suitable plasmid vector comprising HSV sequences using cloning techniques well-known in the art.

It is particularly preferred that the sequence encoding YY1 is operably linked to LAT P2 sequences as described in WO-A-98/30707 (some of the disclosure of which is reproduced above) since this has been shown to dramatically improve long term expression in mammalian cells.

The method of the present involves increasing the level of YY1 mRNA in the cells. Typically this is achieved by delivering DNA encoding YY1 to the cells. As will be readily appreciated the level of YY1 mRNA may also be increased using gene activation technology.

Gene activation involves targeting a promoter upstream of an endogenous gene, with a view to the promoter operating with the endogenous regulatory elements to express the gene. Gene activation involves several steps. First, a targeting construct is produced: this is a polynucleotide containing a promoter (normally a viral promoter) flanked by sequences which allow the promoter to be targeted by homologous recombination to a specific location upstream of the desired endogenous gene. Secondly, the targeting construct is transfected into cells containing the desired gene. Thirdly, the flanking ("or targeting") sequences then undergo homologous recombination, as a result of which the promoter is positioned upstream of the endogenous encoding sequences. Fourthly, the "switched on" gene then expresses the desired protein.

Accordingly in another embodiment of the present invention the composition comprises a DNA sequence comprising a promoter flanked by sequences which target the promoter to a region upstream of the YY1 gene.

As discussed above, the method of the present invention prevents or reduce cellular proliferation. The method of the present invention can therefore be used in the treatment of disease states involving cellular proliferation.

Accordingly, in another aspect the present invention consists in a method of treating or preventing a cellular proliferation disorder in an individual, the method comprising administering to the individual a composition which increases the level of YY1 mRNA in the cells.

In particular embodiments the cellular proliferation disorder is restenosis (particularly following balloon angioplasty), atherosclerosis or cancer, such as prostate or breast cancer.

Following the findings of the present inventors that YY1 is a negative regulator of cellular proliferation the present invention also provides a method of screening for agents which reduce or prevent cellular proliferation.

Accordingly, in a second aspect the present invention consists in a method of screening for compounds which inhibit the proliferation of cells, the method comprising determining the ability of a putative compound to increase induction of YY1, increase expression of YY1 or increase the nuclear accumulation or activity of the YY1 gene product.

In a preferred embodiment of this aspect, the method is performed in vitro.

In a further preferred embodiment the cells are selected from the group consisting of vascular cells, smooth muscle cells, endothelial cells and neoplasia cells.

The putative agent may be tested for the ability to enhance YY1 expression or activity by any suitable means. For example, the test may involve contacting a cell which expresses YY1 with the putative agent and monitoring the production of YY1 mRNA (by, for example, Northern blot analysis) or YY1 protein (by, for example, immnunohistochemical analysis or Western blot analysis). Other suitable tests will be known to those skilled in the art.

As will be appreciated by those skilled in the art, a putative compound which demonstrates the ability to increase induction of YY1, increase expression of YY1 or increase the nuclear accumulation or activity of the YY1 gene product is a potential candidate for development as an antiproliferative drug.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in the specification are herein incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia before the priority date of each claim of this application.

In order that the nature of the present invention may be more dearly understood preferred forms thereof will be described with reference to the following Examples.

Methods

Cell culture—Primary rat aortic smooth muscle cells were obtained from Cell Applications, Inc (San Diego, Calif.) and cultured in Waymouth's medium, pH 7.4, containing 10% fetal bovine serum, 10 U/ml penicillin and 10 µg/ml streptomycin in a humidified atmosphere of 5% $CO_2$ at 37° C. The cells were rendered quiescent by incubation in Waymouth's medium, pH 7.4, containing 0.25% fetal bovine serum for 24 h. The cells were injured by scraping with a sterile stainless steel comb as previously described (15). Cells were not used beyond passage 7 in experiments. Additionally, normal medial vascular smooth muscle cells were derived and characterised from coronary arteries of patients undergoing cardiac transplantation for non-ischaemic cardiomyopathy and human atherosclerotic plaque vascular smooth muscle cells from carotid endarterectomy specimens of patients with symptomatic carotid disease. Cells were cultured to passage 24 before isolation for nuclear extracts.

cDNA array analysis—Differential gene expression between injured and uninjured smooth muscle cells was assessed using Atlas cDNA expression arrays (Clontech Laboratories, Palo Alto, Calif.). Briefly, total RNA (15 µg) was treated with RNase-free DNase I then mRNA was isolated using Poly (A) Quik mRNA isolation kit (Stratagene, La Jolla, Calif.). cDNA was generated from equivalent amounts of mRNA and $^{32}$P-labeled cDNAs were purified using Chromaspin-200 DEPC-water columns provided with the kit. Probes with similar specific activities were hybridized separately to two identical arrays under conditions specified by the manufacturer. Hybridization signals were quantitated using ImageQuant software (Amersham Pharmacia Biotech Ltd., Buckinghamshire, UK).

RT-PCR—Total RNA was prepared from cells that were injured or exposed to FGF-2 with TRIzol in accordance with the manufacturer's instructions (Gibco BRL-Life Technologies, Rockville, Md). RNA was reverse-transcribed to cDNA using oligo dT primers and Superscript (Gibco BRL-Life Technologies, Rockville, Md). PCR was performed using Platinum Taq DNA polymerase (Gibco BRL-Life Technologies, Rockville, Md) with the following amplification conditions: 20mM Tris-HCl (pH 8.4), 50 mM KCl, 1 mM $MgCL_2$, 250 µM dNTP, 0.5 µM primers, 2 µl cDNA and 1 U of Platinum Taq DNA polymerase. For YY1 PCR, cycling conditions were 94° C. for 30 sec, 30 cycles of 95° C. for 10 sec; 53° C. for 30 sec and 72° C. for 1 min. For GAPDH RT-PCR, the same cycling conditions were used except for an annealing temperature of 58° C. and a cycle number of 25. Primer sequences for YY1 were YY1a5 (5'-GAAAACATCTGCA-CACCCACGGTCC-3') (SEQ ID NO:3) and YY1a3 (5'-GTCCTCCTGTTGGGACCACAC-3') (SEQ ID NO:4), whereas those of GAPDH are GAP5 (5'-ACCACAGTCCAT-GCCATCAC-3') (SEQ ID NO:5) and GAP3 (5'-TCCAC-CACCCTGTTGCTGTA-3') (SEQ ID NO:6').

Western blot analysis—Lysates of cells injured or exposed to FGF-2 were resolved by electrophoresis on denaturing 10% SDS-polyacrylamide gels for 2 h at 100V. After transfer of proteins to Immobilon P nylon membranes (Millipore, Bedford, Mass.) and blocking non-specific binding sites with non-fat skim milk, membranes were incubated with mouse monoclonal anti-peptide antibodies targeting YY1 or rabbit polydonal anti-peptide antibodies targeting p53 (Santa Cruz Biotechnology, Santa Cruz, Calif.) (1:1000) prior to chemiluminescence detection (NEN-DuPont). Coomassie-stained gels were destained and photographed to confirm equal loading.

Electrophoretic mobility shift analysis—Nuclear extracts of cells injured or exposed to FGF-2 were prepared as previously described (16). Binding reactions were performed using 10 µg of nuclear extract in 20 µl containing 1 µg of poly(dI.dC)-poly(dI.dC) (Sigma), 12 mM HEPES, pH 7.9, 4 MM Tris-HCl pH 7.9, 1 mM EDTA, 1 mM DTT, 12% glycerol and the $^{32}$P-labeled Oligo MVYY1 (120,000 cpm) or $^{32}$P-labeled Oligo A for 35 min at 22° C. In competition or supershift experiments, the indicated molar excess of unlabelled oligonucleotide or 2 µg of anti-peptide antibody (Santa Cruz Biotechnology, Santa Cruz, Calif.) was included in the binding mixture 10 min prior to addition of the probe. Bound complexes were separated from the unbound probe by nondenaturing 6% PAGE in 1× TBE running buffer at 100V. The gels were vacuum dried and exposed to Hyperfilm-MP (Amersham) overnight at –80° C.

Rat carotid balloon injury—Male Sprague Dawley rats (450-550 g) were anaesthetised with ketamine (60 mg/kg, i.p.) and xylazine (8 mg/kg, i.p.) and the left common and external carotid arteries were exposed via a midline neck incision. A 2F Pogarty balloon catheter (Baxter Healthcare) was introduced into the external carotid, advanced into the common carotid, inflated to generate resistance and withdrawn three times as previously described (16). The catheter was withdrawn and a ligature was applied to the external carotid proximal to the arteriotomy. Animals were sacrificed 4 h after injury by lethal injection of phenobarbitone, and perfusion fixed using 10% (v:v) formaldehyde at 120 mm Hg. The carotids were dissected free, washed with PBS, pH 7.4, placed in OCT (Miles) and frozen in liquid nitrogen. Sections (5 µm) were air-dried, fixed in acetone for 15 min then air-dried. The sections were then exposed to 1% hydrogen peroxide for 20 min, rinsed in PBS, pH 7.4, and incubated with 100 µl of YY1 antibodies (Santa Cruz Biotechnology) (diluted 1:100 in 0.5% BSA/PBS, pH 7.4) for 45 min. The sections were washed with 0.5% Tween 20/PBS, pH 7.4, followed by PBS, pH 7.4 alone, and incubated with 100 µl of biotinylated rabbit anti-mouse secondary antibody (Vector) diluted 1:300 in 0.5% BSA for 30 min. The sections were washed in PBS, pH 7.4 for 5 min prior to incubation in 100 µl of avidin-biotin complex (ABC, Vector) diluted 1:100 in 0.5% BSA for 30 min. The sections were washed again in Tween and PBS as above, and antigen-antibody complexes were detected in 3 min using the diaminobenzidine (DAB) system. Sections were washed in PBS, pH 7.4, counterstained with hematoxylin for 20 sec, dehydrated, cleared and mounted, then visualized by light microscopy and photographed.

FGF-2immunoassay—FGF-2 levels in the supernatant were quantitated using the commercial enzyme-linked immunosorbent assay Quantikine HS human FGF basic immunoassay (R&D Systems, Minneapolis, Minn.).

Transient transfection analysis—Smooth muscle cells were transiently transfected with 5 µg of the chloramphenicol acetyltransferase reporter construct, $(E1)_4TK$-CAT, using FuGENE6 according to the manufacturer's instructions (Roche). FGF-2 was incubated with growth-quiescent cells for 24 h. CAT activity was assessed as previously described (17) and normalized to the concentration of protein in the cell lysates (Biorad Protein Assay).

YY1 overexpression proliferation assay—smooth muscle cells (rat aortic) or endothelial cells (bovine aortic) were grown to 60% confluence in 96-well plates, incubated in serum-free medium for 24 h, then transfected with 1 µg of either pCB6$^+$-YY1 or pCB6$^+$ using FuGENE6, according to the manufacturer's instructions, and incubated for 5 days in the continuous presence of 5% FBS. Plasmid transfection of endothelial and smooth muscle cells with FuGENE6 is extremely efficient (18). The cells were trypsinised and suspensions were quantitated by automated Coulter counter.

Northern blot analysis—Total RNA was isolated from smooth muscle cells or endothelial cells 24 h after transfection with 10 µg of either pCB6$^+$-YY1 or pCB6$^+$ using FuGENE6, and probed with $^{32}$P-labeled YY1 cDNA (generated by PCR using the same primers described above) or $^{32}$P-GAPDH cDNA in Northern blot analysis as previously described (17).

Immunohistochemical detection of YY1, p53, FGF-2 and PCNA in human carotid arteries—Immunohistochemical analysis was performed with antibodies to YY1 (Santa Cruz, sc-7341, final dilution 1:200), p53 (Immunotech, DO-1, dilution 1:50), PCNA (Dako, PC10, dilution 1:50), basic FGF (R&D systems; AB-33-NA, dilution 1:200) and smooth muscle alpha-actin (Novocastra, ASM-1, Dilution 1:25) on consecutive paraffin sections of formalin-fixed atherosclerotic carotid artery specimens obtained at endarterectomy at St. Vincent's Hospital, Sydney. Prior to staining, deparaffinized sections were treated with 3% hydrogen peroxide (peroxidase blocking) and boiled in citrate buffer (pH 6.0) to retrieve antigenicity. The standard avidin-biotin complex (ABC) immunoperoxidase technique was used (19). After washing in Tris-buffered saline (TBS, pH 7.6), sections were incubated in the primary antibody for 60 min, followed by incubation with the appropriate secondary antibody (horse anti-mouse, Vector BA-2000 or goat anti-rabbit, Vector BA-1000) for 20 min, and finally with ABC (Elite Vector PK-6100) for 30 min. Immunogenicity was visualized by treatment in 3,3'-diaminobenzidine (DAB) solution for 2 min, which produced brown coloration. Sections were counterstained with Mayer's haematoxylin. For negative control, the primary antibody was omitted or the sections were treated with the immunoglobulin fraction of suitable non-immune serum as a substitute for the primary antibody. No positive staining was observed in any of the negative control sections.

Results and Discussion

YY1 expression and binding activity is induced in smooth muscle cells in response to injury—In efforts to identify new genes that are activated following mechanical injury in vascular smooth muscle cells, we reverse-transcribed (RT) mRNA isolated from mechanically-injured and uninjured growth-quiescent aortic smooth muscle cells and compared the expression of specific genes by hybridization with spatially addressable cDNA arrays. We previously demonstrated that the immediate-early gene and transcription factor early growth response factor-1 (Egr-1) is rapidly induced by injury using a well-established in vitro scraping model (15). YY1 transcript levels, like those of Egr-1, increased several-fold within 1 h of injury (FIG. 1). In contrast, alpha-tubulin mRNA expression did not change in response to injury.

We next performed RT-PCR analysis using primers directed to elements within the coding region to confirm that YY1 mRNA is inducibly expressed following mechanical injury. YY1 was basally expressed in uninjured smooth muscle cells. Injury increased YY1 expression within 2 h of injury and levels remained elevated after 4 h. Western immunoblot analysis using monoclonal antibodies targeting YY1 produced a single protein species with a relative molecular mass (Mr) of 68 kDa, which corresponds to the expected Mr of YY1 (20). YY1 protein, like YY1 mRNA was basally expressed and levels increased upon mechanical injury.

To determine whether changes in YY1 mRNA and protein expression after mechanical injury correlate with the binding activity of this transcription factor, we performed electrophoretic mobility shift analysis (EMSA) using $^{32}$P-labeled Oligo MVYY1, a double-stranded oligonudeotide bearing consensus binding element for YY1 from the upstream conserved region of the Moloney murine leukemia gene (9). A major nucleoprotein complex of weak intensity was detected using nuclear extracts of uninjured cells. The intensity of this complex increased significantly within 1 h of injury and levels remained high after 4 h. To confirm the integrity of these extracts, we performed EMSA using $^{32}$P-labeled Oligo A, whose sequence derives from the proximal PDGF-A promoter and contains overlapping consensus binding elements for Egr-1. Egr-1 binding activity increased within 1 h of injury, as previously demonstrated in a different vascular cell type (21) and consistent with FIG. 1.

To demonstrate the specificity of the nucleoprotein complex obtained using $^{32}$P-Oligo MVYY1, we incubated the extracts with increasing amounts of unlabeled oligonudeotide. This resulted in dose-dependent inhibition of the inducible complex and virtually complete inhibition at a 25-fold excess. In contrast, the same fold excess of unlabeled Oligo A had no effect of the intensity of this complex. To elucidate the identity of the protein component of the inducible complex, we performed supershift analysis. Incubation of the nuclear extracts with YY1 antibodies used for Western blot analysis prior to the addition of $^{32}$P-Oligo MVYY1 eliminated the formation of the complex, instead producing a supershift. In contrast, when an identical amount of Egr-1 antibodies were used for preincubation, the complex was completely unaffected. These data provide the first demonstration that YY1 mRNA and protein are increased in vascular smooth muscle cells upon mechanical injury.

YY1 expression induced in balloon injured rat carotid arteries—To determine whether the induction of YY1 by mechanical injury in vitro is also observed following injury to the intact vessel wall, we performed balloon angioplasty to the left common carotid arteries of Sprague-Dawley rats. Immunohistochemical analysis with YY1 antibodies revealed that YY1 is weakly expressed by smooth muscle cells in the medial compartment of the artery wall. The intensity of staining increased significantly in the media within 4 h of balloon injury. The specificity of staining was evidenced by our inability to observe YY1 signal when primary (YY1) antibody was omitted from the protocol. These data demonstrate for the first time the induction of YY1 in the injured artery wall.

Figure 2:
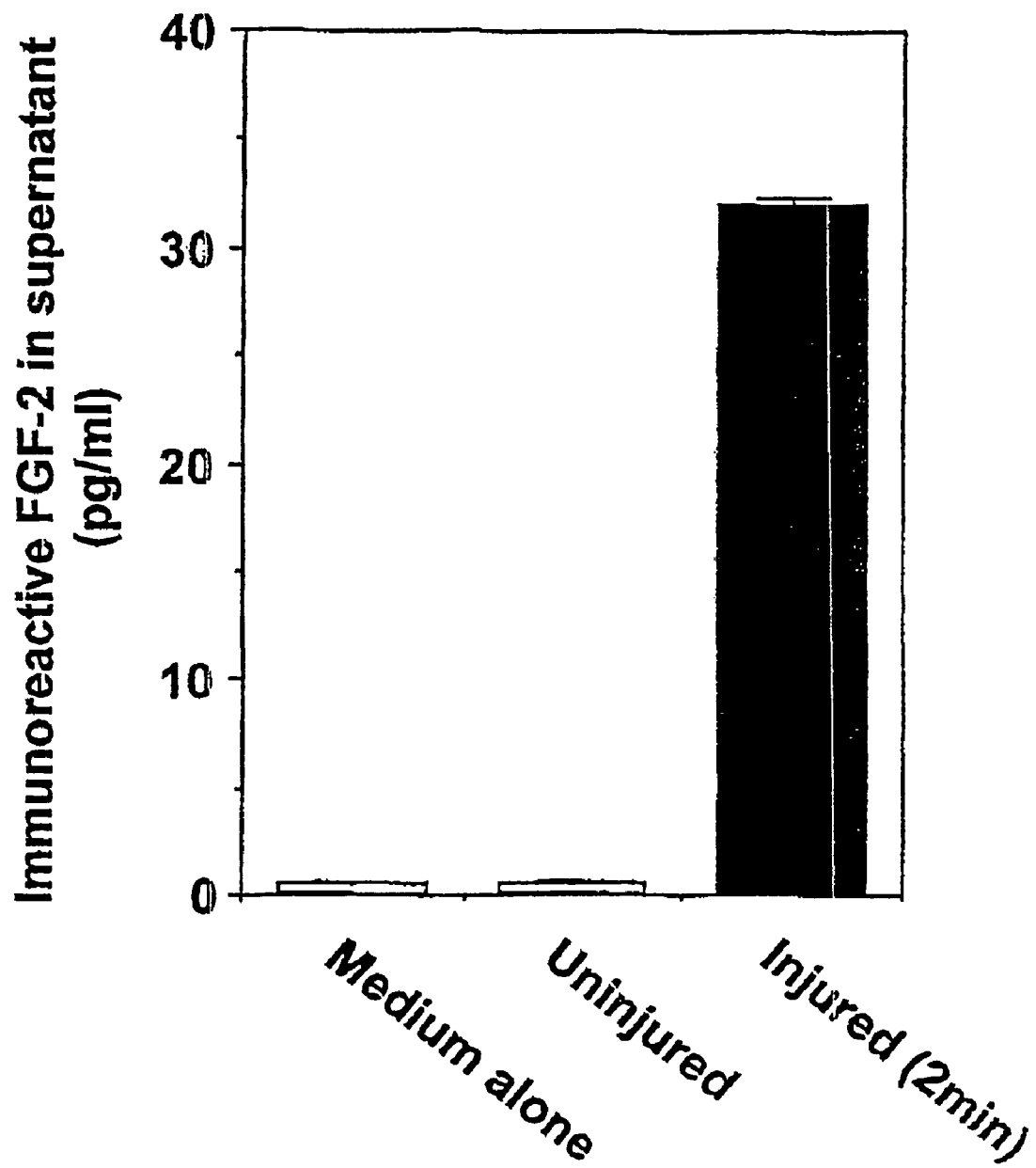
FIG. 2. FGF-2 stimulates YY1 expression, binding and transcriptional activity in growth-quiescent vascular smooth muscle cells. Endogenous FGF-2 is released from growth-quiescent vascular smooth muscle cells within minutes of scraping. FGF-2 levels in the culture medium were measured (before and 2 min after scraping) using a commercial ELISA specific for FGF-2. (Quantikine, R&D Systems) using recombinant PGF-2 as the standard.

FGF-2 stimulates YY1 expression, binding and transcriptional activity—We hypothesized that the activation of YY1 following injury is regulated by endogenous factors released from the cells themselves. We focused on FGF-2 since FGF-2 mRNA and protein are basally expressed in vascular smooth cells in culture as well as in the intact artery wall. We measured levels of FGF-2 in the supernatant of cultured growth-quiescent smooth muscle cells by ELISA before and after scraping. Immunoreactive FGF-2 was barely detectable in the culture medium or supernatant of undisturbed smooth muscle cells (FIG. 2). However, FGF-2 levels increased dramatically within 2 min of injury (FIG. 2). This led us to explore the possibility that FGF-2 may regulate the expression of YY1, hitherto unreported in any cell type.

YY1 MRNA expression increased in vascular smooth muscle cells exposed to FGF-2. RT-PCR analysis revealed that YY1 transcript levels increased within 1 h of exposure to the growth factor and remained elevated even after 24 h. Western immunoblot analysis confirmed these findings of inducible YY1 expression at the level of protein.

To address the spatial distribution of inducible YY1 protein expression we performed in situ immunofluorescence analysis using YY1 antibodies as the primary antibody with secondary antibodies tagged with fluorescein isothiocyanate (FITC). YY1 immunoreactivity was preferentially detected in the nuclei of a small proportion of smooth muscle cells. After 1 h or 4 h of exposure to FGF-2, considerable greater proportion of cell nuclei showed immunofluorescence for YY1 protein. The specificity of the system was confirmed by the inability to detect immunofluorescence when the YY1 antibody was omitted.

We next used EMSA to demonstrate whether FGF-2-inducible YY1 expression protein produced increased DNA-binding activity. FGF-2 increased YY1 DNA-binding activity within 1 h and levels remained elevated after 4 h, similar to our earlier observations using nuclear extracts of cells that had been injured. Unlike the rapid transient induction of Egr-1 after injury, however, Egr-1 binding activity was more sustained in cells exposed to FGF-2.

To demonstrate that YY1 binding activity induced by FGP-2 was functionally significant, we exposed smooth muscle cells transfected with the chloramphenicol acetyl-transferase (CAT)-based reporter construct $(E1)_4TK$-CAT, which contains four copies of a high affinity YY1 binding site upstream of the thymidine kinase (TK) promoter (22), to FGF-2. This construct has previously been used to gauge YY1 binding activity in an overexpression setting in murine fibroblasts (22). FGF-2 stimulated CAT reporter expression within 24 h in a dose-dependent manner (FIG. 2F). Taken together, these findings demonstrate that FGF-2 induces YY1 mRNA and protein expression, DNA-binding activity and can trans-activate gene expression in vascular smooth muscle cells.

YY1 induction by injury is mediated by FGF-2release—Since injury causes the rapid release of FGF-2 from smooth muscle cells, and that injury and recombinant FGF-2 each stimulate YY1 expression in this cell type, we finally determined whether the inducible expression of YY1 following injury is mediated by the local effect of endogenous FGF-2. We therefore incubated growth-quiescent smooth muscle cells with neutralizing FGF-2 antibodies prior to scraping, then assessed YY1 levels by Western immunoblot analysis. Injury increased YY1 protein levels within 2 h. Interestingly, levels of the transcription factor were significantly reduced in the lysates of cells preincubated with FGF-2 antibodies. In contrast, isotype and species-matched immunoglobulin has no appreciable effect on injury-inducible YY1 protein expression. These findings demonstrate the paracrine effect of endogenous FGF-2 in the increased expression of YY1 in smooth muscle cells following mechanical injury.

Differential YY1 expression in atherosclerotic plaque and normal medial smooth muscle cells—Many genes whose products have been implicated in the progression of lesions of atherosclerosis and post-angioplasty restenosis are repressed by YY1 at the level of transcription (9-14,23). We hypothesized that YY1 expression would be greater in smooth muscle cells in the medial compartment of the artery wall compared with those in the atherosclerotic lesion. Western blot analysis revealed that YY1 is poorly expressed in smooth muscle cells derived from the atherosclerotic lesions of two patients who had undergone carotid endarterectomy. Conversely, YY1 immunoreactivity was readily detectable in medial smooth muscle cells derived from the arteries of 4 patients with no histological evidence of disease. In contrast, p53, a second transcriptional repressor, was present in intimal smooth muscle cells but was virtually undetectable in medial cells, consistent with previous reports of increased p53 expression (24) and apoptosis (25) in intimal cells compared with the media.

Figure 3:
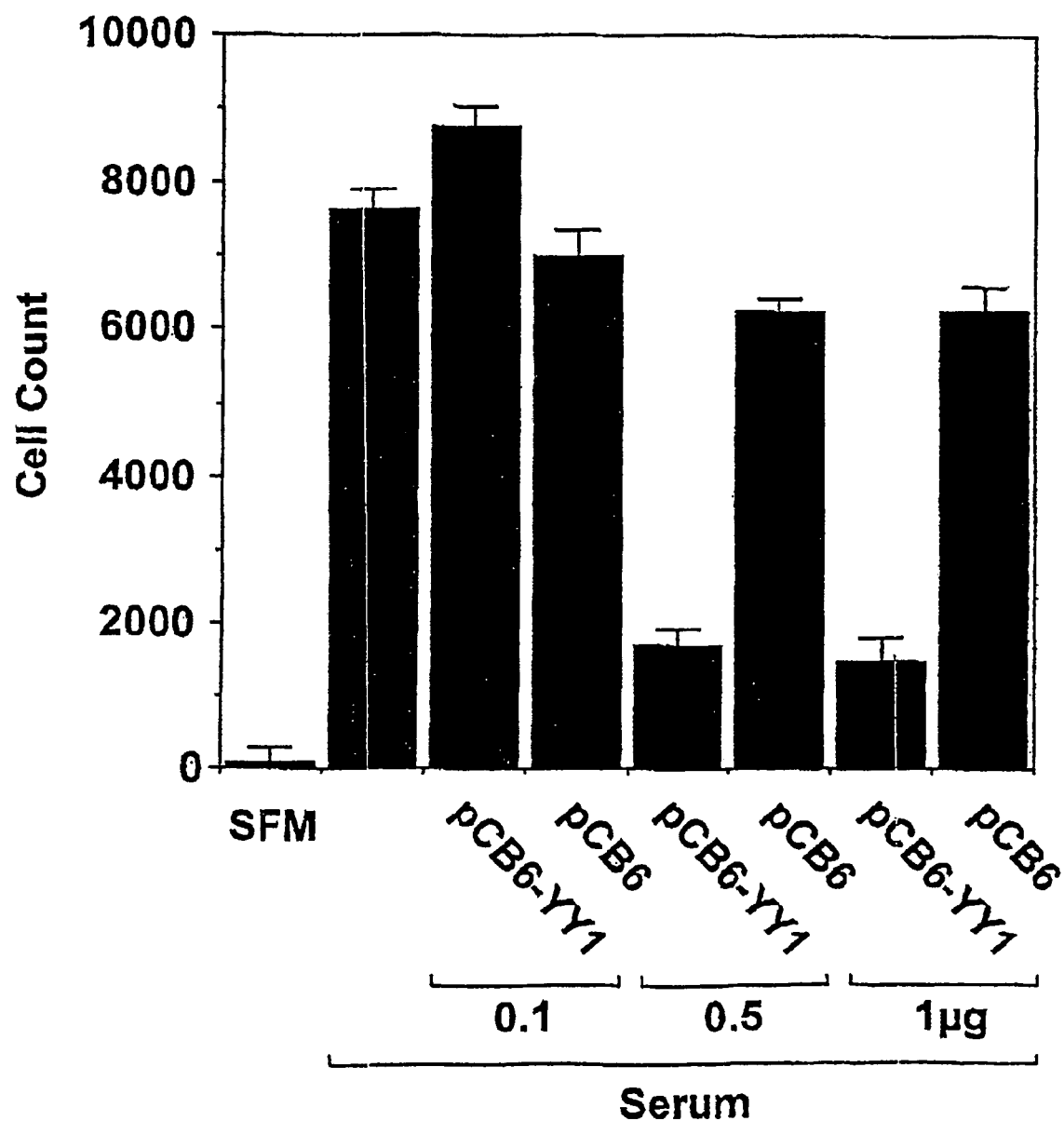
FIG. 3. YY1 inhibits vascular smooth muscle cell proliferation. Subconfluent growth-quiescent rat aortic smooth muscle cells in 96-well plates were transfected with the indicated amounts of either pCB6$^+$-YY1 or pCB6$^+$ using FuGENE6. The cells were trypsinised and suspensions were quantitated using an automated Coulter counter after 5 days in the continuous presence of 5% FBS.

Overexpression of YY1 suppresses cellular proliferation—Since YY1 can repress the expression of growth factor genes, we determined whether YY1 could influence smooth muscle cell replication. Incubation of sub-confluent growth-quiescent smooth muscle cells in medium containing serum, as expected, increased the number of cells in this population (FIG. 3). Cells transfected with 0.5 µg of a CMV-driven YY1 expression vector, pCB6$^+$-YY1, strongly inhibited serum-inducible smooth muscle cell proliferation (FIG. 3). In contrast, cell replication in the cohort transfected with an identical amount of the empty vector (pCB6$^+$) increased in the presence of serum (FIG. 3). YY1 inhibition of smooth muscle cell proliferation was dose-dependent. To demonstrate that YY1 was indeed expressed, we performed Northern blot analysis on RNA isolated from smooth muscle cells transfected with pCB6$^+$-YY1. This showed strong expression of exogenous YY1 MRNA 24 h after plasmid transfection. These findings indicate that YY1 is a potent inhibitor of vascular smooth muscle cell proliferation, consistent with preferential YY1 expression in the growth-quiescent media. YY1 transfection failed to inhibit the proliferation of human microvascular endothelial cells (HMEC-1 or bovine aortic endothelial cells (BAEC), but did inhibit the growth of human foreskin fibroblasts (HFF), human prostate cancer cells (PC3), and human breast cancer cells (MCF7). To date, YY1 has not been directly linked to cell replication in any cell type.

YY1 and FGF-2 expression in human atherosclerotic tissue—Since FGF-2 positively regulates YY1 expression, we hypothesized that YY1 and FGF-2 would co-localize in the arterial wall. Immunohistochemical staining revealed that YY1 was strongly expressed by alpha-actin positive smooth muscle cells in the arterial media compared with weak expression in the intima. YY1 staining in the media was distributed mosaically and was exclusively nuclear. In contrast, p53 was expressed in the intima. FGF-2 immunoreactivity was detected in the nuclear and cytoplasmic compartments of medial smooth muscle cells, consistent with previous observations in fibrous lesions (26,27). FGF-2 immunoreactivity was coincident with YY1 expression.

Finally, we reasoned that since YY1 inhibits smooth muscle cell replication (FIG. 3), YY1 expression in the artery wall would inversely correlate with mitogenicity. PCNA staining was accordingly confined to smooth muscle cells and occasional macrophages in the intima, with few PCNA-expressing cells detected in the media.

The mechanisms governing the activation of the YY1 gene expression are presently unknown. In smooth muscle cells, YY1 has been found to physically associate with (28,29) and activate the smooth muscle cell-specific SMC22-alpha promoter (28), but has not yet been reported to be induced by defined extracellular stimuli in this cell type. YY1 repressor activity is induced in cardiac myocytes exposed to interleukin-1 (30) and in osteosarcoma cells incubated with vitamin D (5). The human YY1 promoter has been cloned from a liver genomic library and contains a single transcriptional initiation site located 478 bp upstream of the AUG translational start site (31). Among several putative nucleotide recognition elements for known transcriptional regulators is a consensus site for CREB/ATF and three tandem sites for Myb (31). Cyclic-AMP response elements can mediate transcriptional activation by FGF-2 (32). Similarly, FGF-2 can stimulate the expression of Myb factors (33) which can potentiate FGF-inducible proliferation (34). Therefore, our present demonstration of increased YY1 expression in smooth muscle cells exposed to FGF-2 may be due to the activity of these positive regulatory transcription factors. The spatial relationship established between FGF-2 and YY1 in lesions in this paper may be representative of other settings. Interestingly, FGF-2, and other members of the FGF family, are expressed in the early stages of embryonal development (35), consistent with peri-implantation lethality in mice deficient in YY1 gene (36).

We observed approximately a three-fold increase in YY1 mRNA and protein expression as well as DNA-binding and transcriptional activity with FGF-2. This magnitude induction may be sufficient to influence gene expression at local sites of FGF-2 release in the vasculature. Indeed, as little as a two-fold induction in endogenous YY1 expression can lead to significant transcriptional repression in cardiac myocytes which is entirely dependent on the integrity of the zinc finger structure of YY1 (30). In other contexts, minor changes in DNA binding activity can have profound effects on the transcriptional activity of dependent genes (37).

Changes in smooth muscle phenotype as a consequence of local FGF-2 release are likely to depend on the net effect of positive and negative influences at the signaling and transcriptional level. We previously demonstrated that FGF-2 induces the expression of early growth response factor-1 (Egr-1) which activates the expression of many genes implicated in the initiation and progression of atherosclerosis and restenosis (15). In vascular endothelial cells, the induction of Egr-1 after injury is blocked by antibodies targeting FGF-2 (21). These data demonstrate that FGF-2 can stimulate the expression of two very different kinds of transcription factors, namely YY1 the repressor and Egr-1 the activator. It is the complex interplay of transcription factors at promoter elements that dictate gene expression and changes in cell movement, proliferation and adhesion in the injured vessel wall.

We demonstrate here for the first time that YY1 expression and DNA-binding activity increase in vascular smooth muscle cells within hours of mechanical injury. We have also shown that FGF-2 is a positive regulator of YY1 expression, and moreover, that endogenous FGF-2 accounts for the induction of YY1 after injury. The present study demonstrates the yin yang nature of YY1. On the one hand, YY1 expression is under the direct control of FGF-2 which stimulates smooth muscle cell growth. On the other, YY1 can inhibit smooth muscle cell growth. That YY1 and FGF-2 are co-expressed in growth-quiescent smooth muscle cells in human arteries suggests that YY1 may restrict pro-atherogenic gene expression and cell growth in the injured vessel wall. Since the adaptive response to arterial cell injury involves a dramatic increase in smooth muscle cell replication, the sustained activation of this enigmatic transcription factor may help restrict what otherwise may result in greater smooth muscle cell mitogenesis in early atherogenesis.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of preventing or reducing cellular proliferation of smooth muscle cells, breast cancer cells or prostate cancer cells, the method comprising locally administering to smooth muscle cells, breast cancer cells or prostate cancer cells a composition comprising a nucleic acid sequence encoding human YY1 comprising the amino acid sequence as set forth in SEQ ID NO: 2, the nucleic acid sequence being operatively linked to control sequences which promote expression of YY1, wherein administering the composition to the smooth muscle cells results in expression of YY1 in said smooth muscle cells, thereby preventing or reducing cellular proliferation of the smooth muscle cells; wherein administering the composition to the breast cancer cells results in expression of YY1 in said breast cancer cells, thereby preventing or reducing cellular proliferation of the breast cancer cells; and wherein administering the composition to the prostate cancer cells results in expression of YY1 in said prostate cancer cells, thereby preventing or reducing cellular proliferation of the prostate cancer cells.

2. The method according to claim 1 wherein the composition further comprises a pharmaceutically acceptable carrier.

3. The method according to claim 2 wherein the nucleic acid sequence is SEQ ID NO: 1.

4. The method according to claim 1 wherein the nucleic acid sequence is contained within a vector.

5. The method according to claim 4 wherein the vector is an adenovirus.

6. The method according to claim 5 wherein the vector is an Ad2 or an Ad5 adenovirus.

7. A method of treating or preventing restenosis, atherosclerosis or cancer in an individual, the method comprising administering to smooth muscle cells, breast cancer cells or prostate cancer cells of the individual a composition comprising a nucleic acid sequence encoding YY1 comprising the amino acid sequence as set forth in SEQ ID NO: 2, the nucleic acid sequence being operatively linked to control sequence which promote expression of YY1, wherein administering the composition to the smooth muscle cells results in expression of YY1 in said smooth muscle cells, thereby preventing or reducing cellular proliferation of the smooth muscle cells; wherein administering the composition to the breast cancer cells results in expression of YY1 in said breast cancer cells, thereby preventing or reducing cellular proliferation of the breast cancer cells; and wherein administering the composition to the prostate cancer cells results in expression of YY1 in said prostate cancer cells, thereby preventing or reducing cellular proliferation of the prostate cancer cells.

8. The method according to claim 7, wherein the restenosis follows balloon angioplasty.

9. An angioplastic stent for inhibiting onset of restenosis comprising an angioplastic stent operably coated with a prophylactically effective dose of a composition comprising a nucleic acid sequence encoding human YY1 comprising the amino acid sequence as set forth in SEQ ID NO: 2, the nucleic acid sequence being operatively linked to control sequences which promote expression of YY1.

10. The angioplastic stent according to claim 9 wherein the composition further comprises a pharmaceutically acceptable carrier.

11. The angioplastic stent according to claim 10 wherein the nucleic acid sequence is SEQ ID NO: 1.

12. The angioplastic stent according to claim 9 wherein the nucleic acid sequence is contained within a vector.

13. The angioplastic stent according to claim 12 wherein the vector in an adenovirus.

14. The angioplastic stent according to claim 13 wherein the vector is an Ad2 or an Ad5 adenovirus.

15. A method for inhibiting the onset of restenosis in a subject undergoing angioplasty comprising administering the stent according to claim 9 to the lumen site of potential restenosis of the subject at around the time of angioplasty.

* * * * *